(12) United States Patent
Pointer et al.

(10) Patent No.: US 9,834,365 B2
(45) Date of Patent: Dec. 5, 2017

(54) TEMPERATURE STABILIZING CARGO COMPARTMENT, INCLUDING A FREEZE AND HEAT BARRIER, FOR TRANSPORT CONTAINER CONSTRUCTED WITH THERMAL RESISTANT MATERIALS

(71) Applicant: ECO-PIM Technologies, Brighton, MI (US)

(72) Inventors: Robin L Pointer, Saint Clair Shores, MI (US); P. Mario DiNello, Ray Township, MI (US); Joseph Altomonte, Grandville, OH (US); Robert C Raymond, Pickerington, OH (US)

( * ) Notice: Subject to any disclaimer, the term of this patent is extended or adjusted under 35 U.S.C. 154(b) by 1250 days.

(21) Appl. No.: 13/686,679

(22) Filed: Nov. 27, 2012

(65) Prior Publication Data

US 2014/0144161 A1    May 29, 2014

Related U.S. Application Data

(60) Provisional application No. 61/628,157, filed on Oct. 24, 2011.

(51) Int. Cl.
| F25D 23/06 | (2006.01) |
| A61M 5/32 | (2006.01) |
| B65D 81/38 | (2006.01) |
| D06M 16/00 | (2006.01) |

(Continued)

(52) U.S. Cl.
CPC ......... *B65D 81/3823* (2013.01); *B65D 81/38* (2013.01); *B65D 81/3858* (2013.01);

(Continued)

(58) Field of Classification Search
CPC ............... B65D 81/3823; B65D 81/38; B65D 81/3813; B65D 81/3818; B65D 81/382;

(Continued)

(56) References Cited

U.S. PATENT DOCUMENTS

| 2,971,640 A | * | 2/1961 | Snelling | ............... B65D 81/113 |
| | | | | 206/524 |
| 4,745,015 A | * | 5/1988 | Cheng | ..................... B32B 15/08 |
| | | | | 105/357 |

(Continued)

*Primary Examiner* — Frantz Jules
*Assistant Examiner* — Erik Mendoza-Wilkenfel

(57) ABSTRACT

Novel method of preserving the internal environmental air temperature and thereby stabilizing the temperature within the cargo compartment of a transport container, and thereby protecting the cargo itself from degradation due to temperature fluxuations, including a freeze and heat barrier attained through the characteristics of the article of manufacture, composition of matter, and method of preservation of the internal environmental air temperature and proximate cargo within said cargo compartment; along with a machine or devise that is used as either a stand-alone container, or as an insert to retrofit existing containers so as to make said retrofitted devices capable of providing cooling over an extended period of time are disclosed. The inserted cargo compartments described herein are particularly useful for temperature-stabilizing cargo compartment shipping containers that are required to maintain a temperature below ambient for a time sufficient to complete delivery of the container and its contents. The shipping containers can be utilized to cost-effectively transport temperature-sensitive products.

9 Claims, 6 Drawing Sheets

EXPLODED VIEW OF VIP, PIR, OR OTHER TRM LAYERED SHIPPING TRANSPORT

(51) Int. Cl.
  *C23C 8/06* (2006.01)
  *B65D 90/04* (2006.01)
  *B65D 90/06* (2006.01)

(52) U.S. Cl.
  CPC ....... *B65D 81/3862* (2013.01); *B65D 90/041* (2013.01); *B65D 90/06* (2013.01); *C23C 8/06* (2013.01); *D06M 16/00* (2013.01); *F25D 23/06* (2013.01); *A61M 5/32* (2013.01); *Y10T 428/231* (2015.01); *Y10T 428/24149* (2015.01); *Y10T 428/24628* (2015.01); *Y10T 428/249956* (2015.04)

(58) Field of Classification Search
  CPC ............ B65D 81/3825; B65D 81/3832; B65D 81/3834; B65D 81/3848; B65D 81/3855; B65D 81/3858; B65B 90/06; B65B 90/041; F25D 23/062; D06M 11/55; C23C 8/06; A61M 5/32; A45C 11/20; A61J 1/00; A61J 1/06
  See application file for complete search history.

(56) References Cited

U.S. PATENT DOCUMENTS

| | | | | |
|---|---|---|---|---|
| 5,238,750 | A * | 8/1993 | Niehaus | B32B 7/02 428/513 |
| 5,520,644 | A * | 5/1996 | Imran | A61M 25/0144 338/128 |
| 2006/0113307 | A1* | 6/2006 | Goulette | A45C 11/20 220/495.06 |
| 2008/0135564 | A1* | 6/2008 | Romero | B65D 81/3827 220/592.2 |
| 2009/0145911 | A1* | 6/2009 | Hyde | B65D 81/3802 220/592.21 |
| 2010/0064720 | A1* | 3/2010 | Fuchs | F25C 1/22 62/457.7 |
| 2010/0314397 | A1* | 12/2010 | Williams | B65D 81/3823 220/592.01 |
| 2011/0147391 | A1* | 6/2011 | Corder | A61J 1/165 220/592.27 |

* cited by examiner

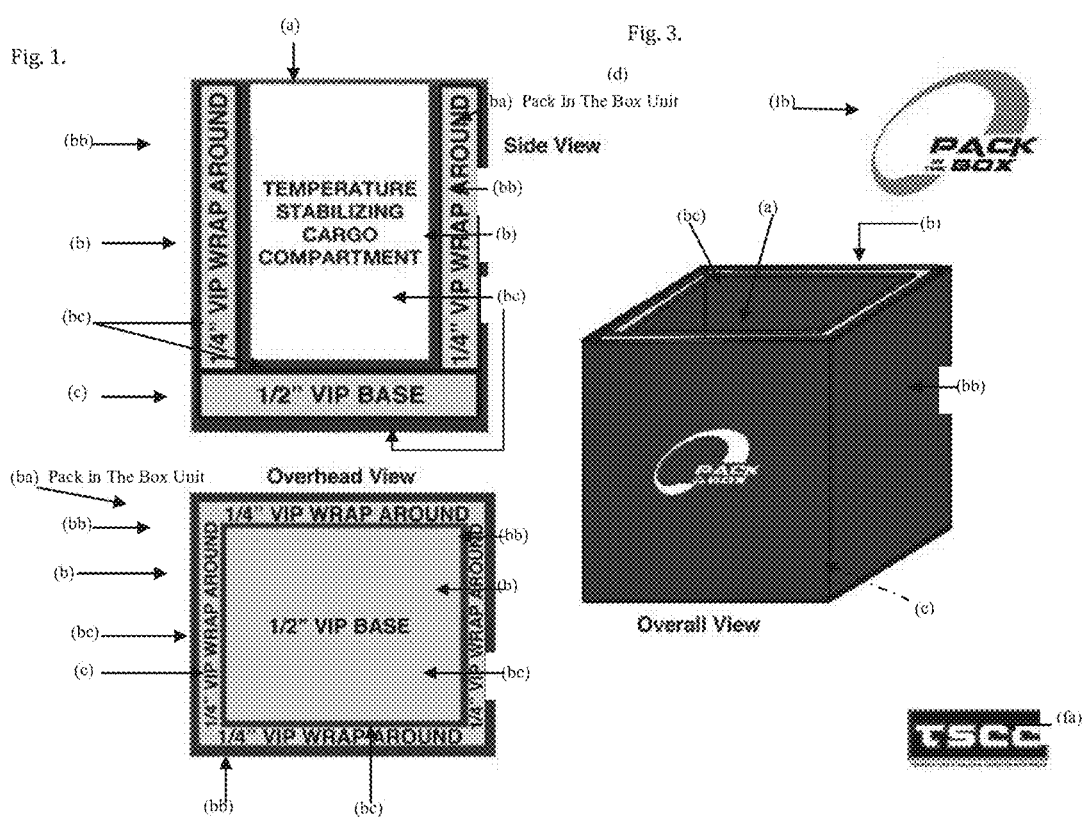

Fig. 4. PACK IN THE BOX ONE PIECE FOLDED DESIGN
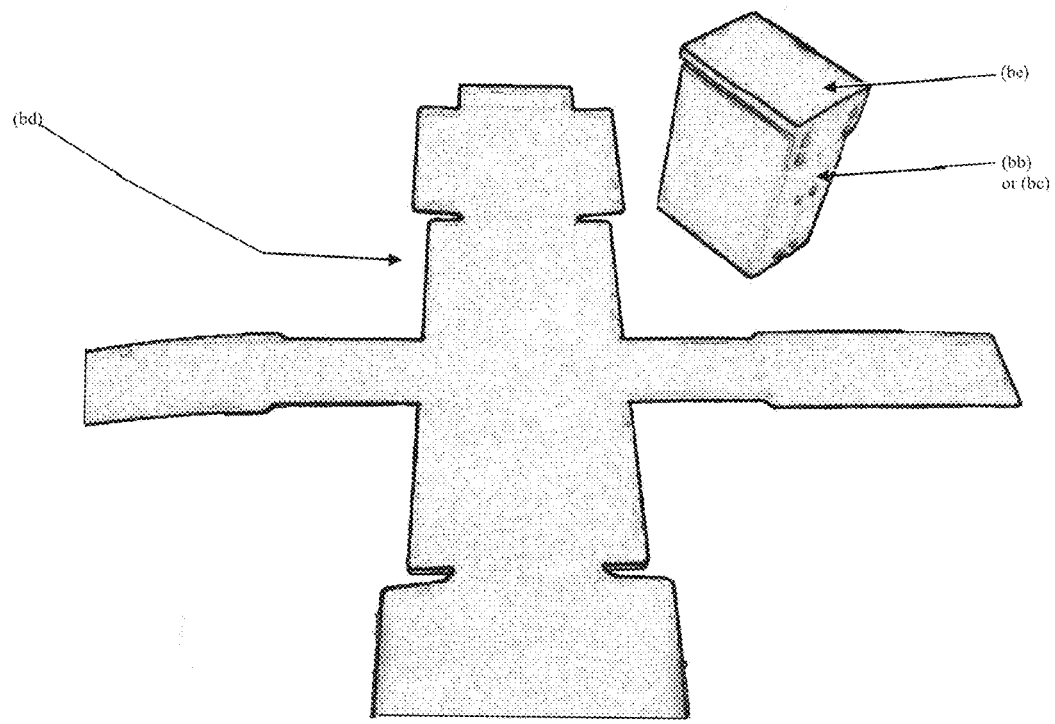
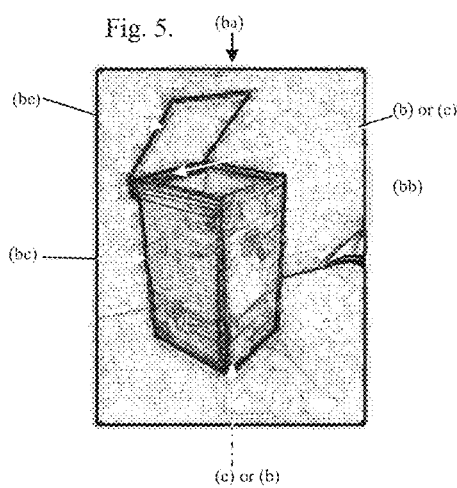
Fig. 5.
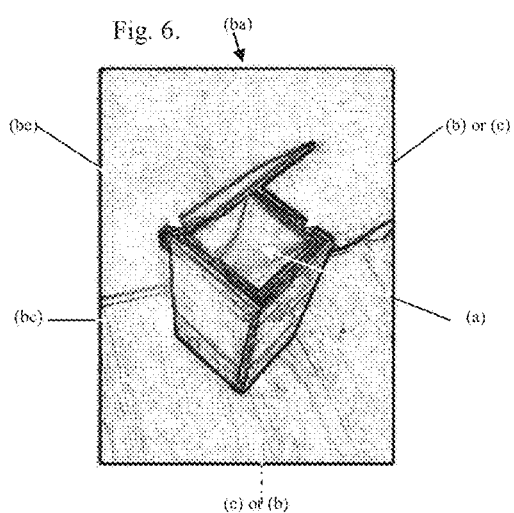
Fig. 6.

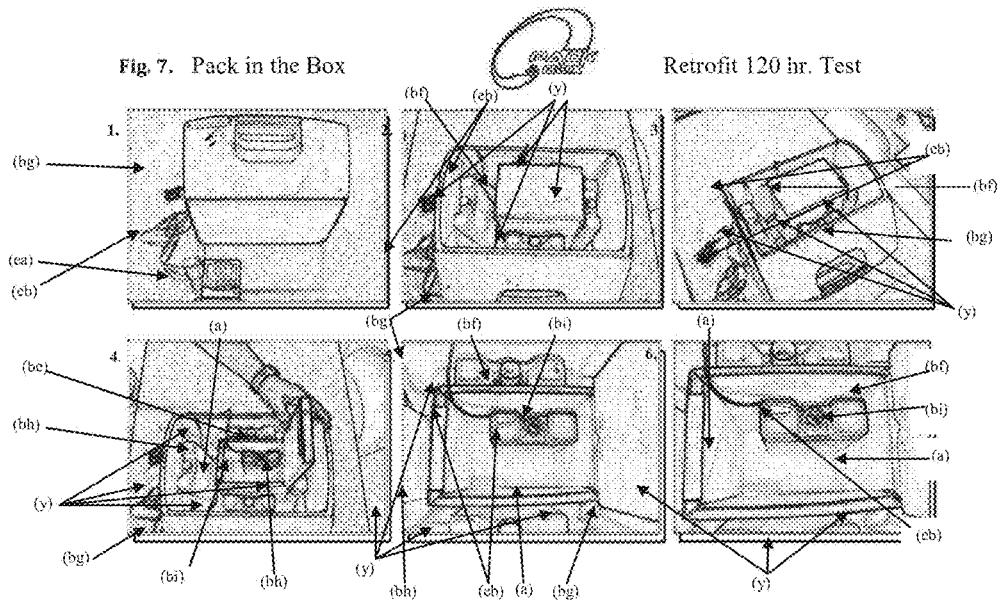
Fig. 7. Pack in the Box    Retrofit 120 hr. Test
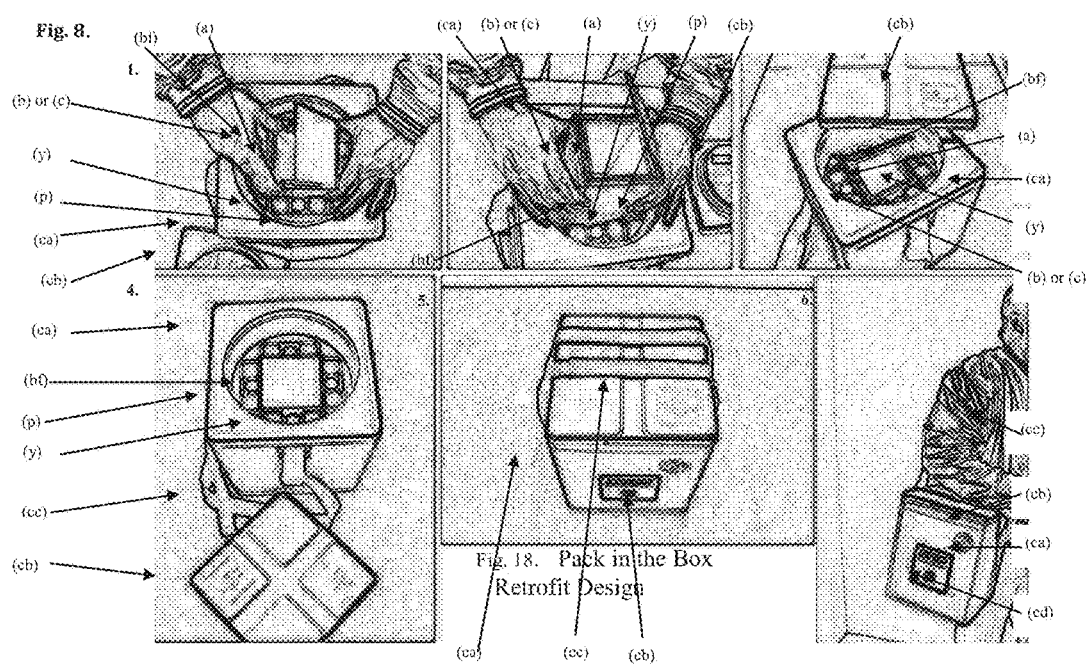
Fig. 8.
Fig. 18. Pack in the Box Retrofit Design Fig. 9. (bf) Pack in the Box Retrofit
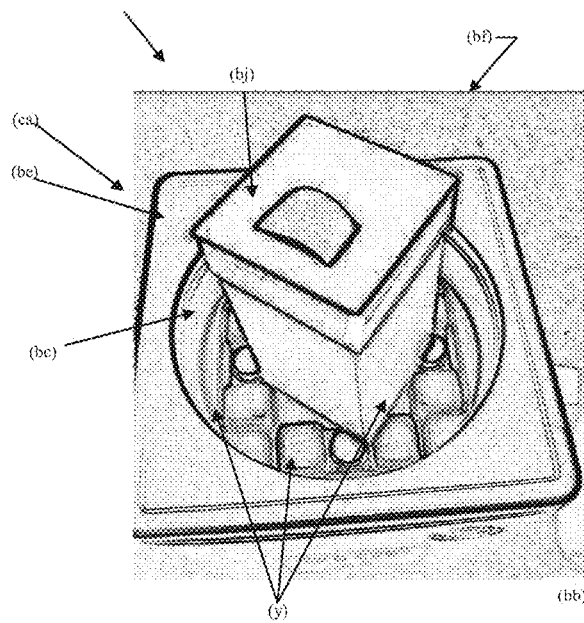
Fig. 10. TSCC in Pack in the Box
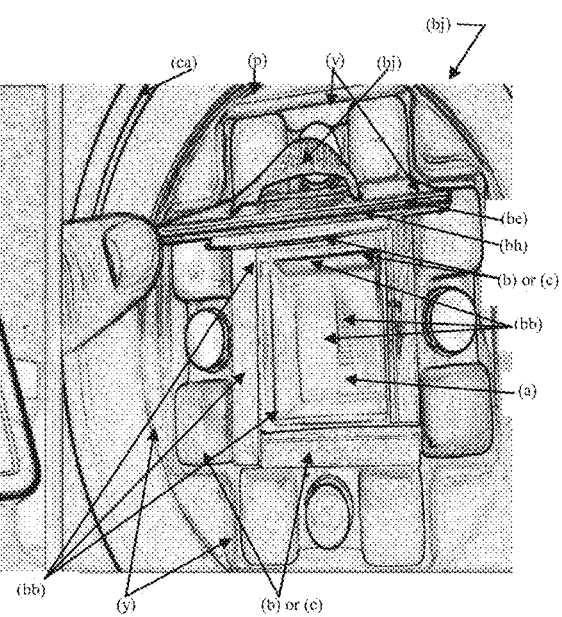

Fig. 11.
EXPLODED VIEW OF VIP, PIR, OR OTHER TRM LAYERED SHIPPING TRANSPORT
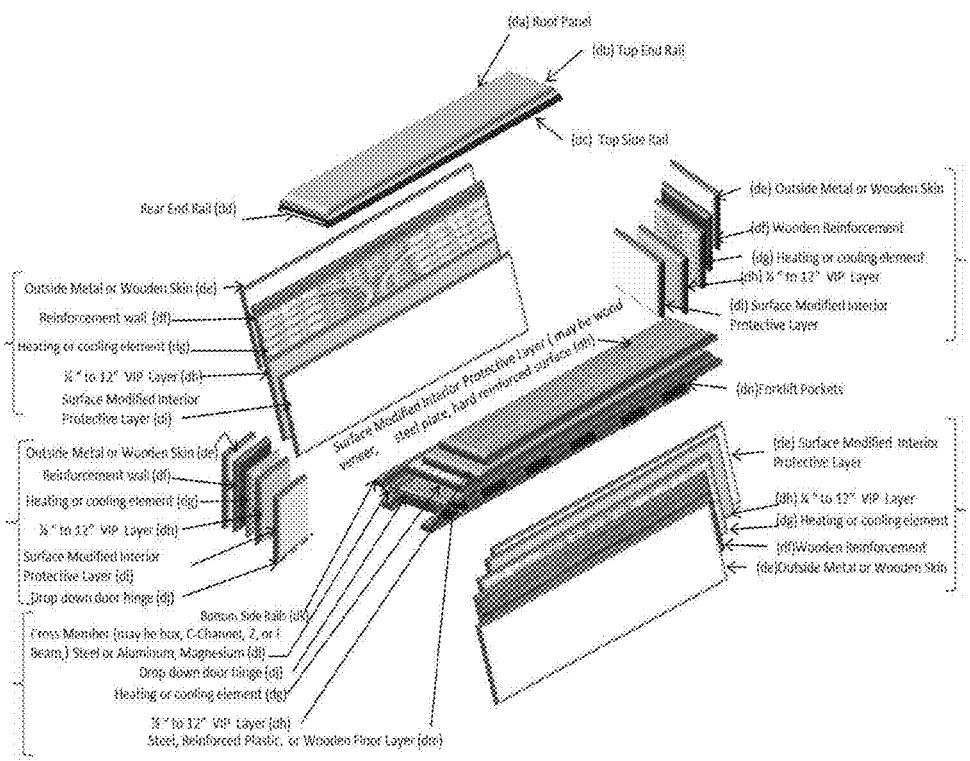
Fig. 12. SHIPPING CONTAINER AND INSERT OF TSCC
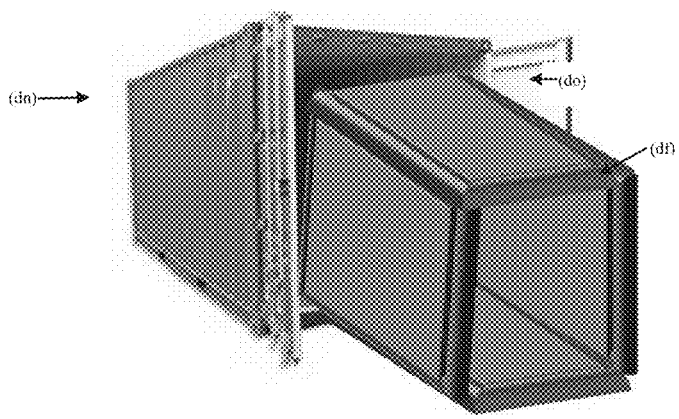

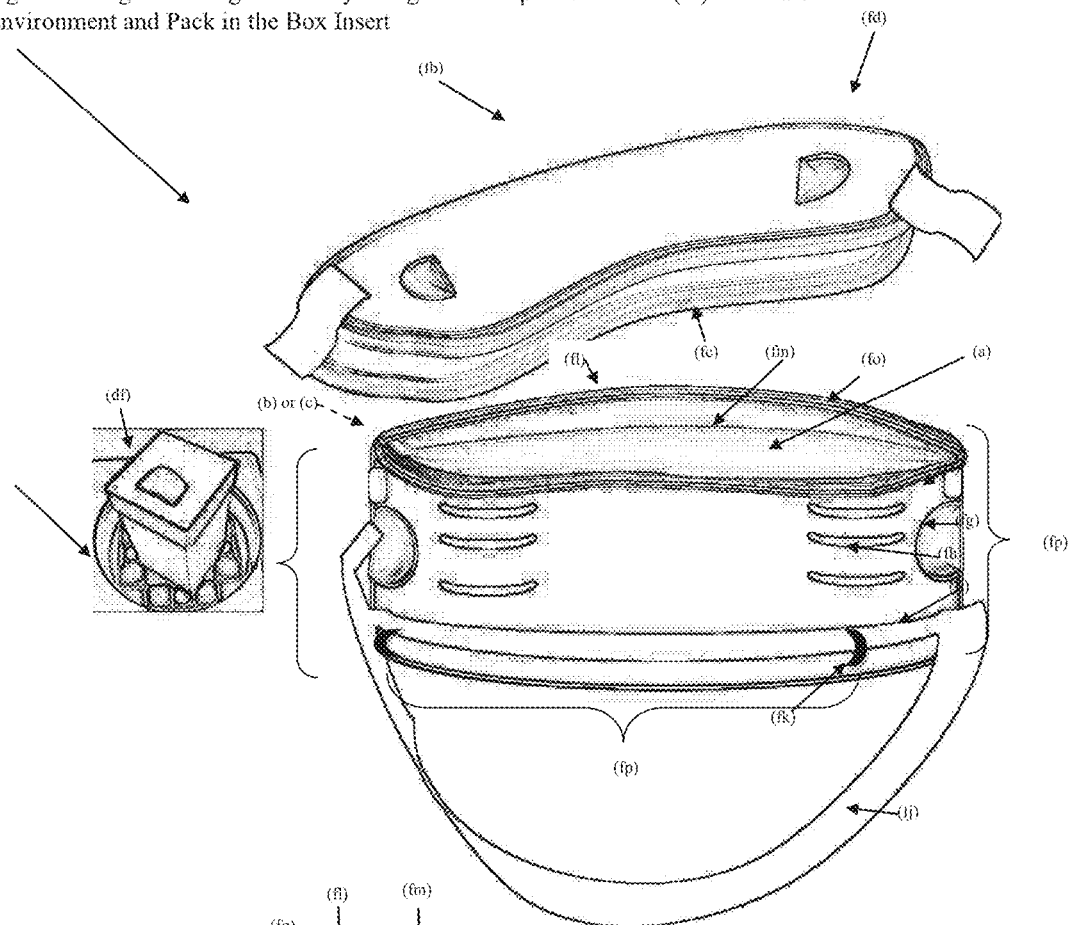
Fig. 13. Diagram of Ergonomically Designed Transport Container (fa) with TSCC Environment and Pack in the Box Insert
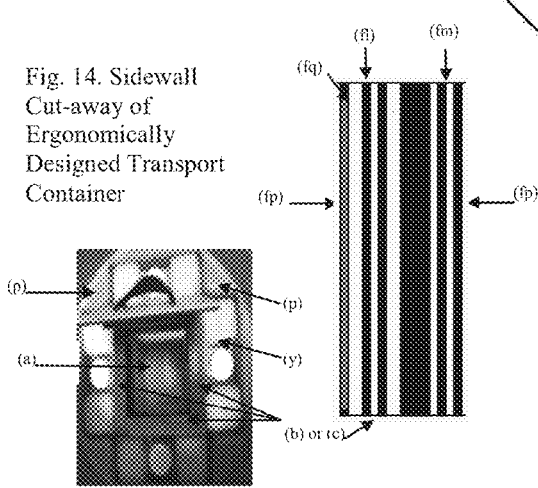
Fig. 14. Sidewall Cut-away of Ergonomically Designed Transport Container

TEMPERATURE STABILIZING CARGO COMPARTMENT, INCLUDING A FREEZE AND HEAT BARRIER, FOR TRANSPORT CONTAINER CONSTRUCTED WITH THERMAL RESISTANT MATERIALS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Description of Related Art Including Information Disclosed Under 37 CFR 1.97 and 1.98

(1) No item of information contained in the information disclosure statement was first cited in any communication from a foreign patent office in a counterpart foreign application not more than three months prior to the filing of the information disclosure statement; or
(2) No item of information contained in the information disclosure statement was cited in a communication from a foreign patent office in a counterpart foreign application, and, to the knowledge of the person signing the certification after making reasonable inquiry, no item of information contained in the information disclosure statement was known to any individual designated in §1.56(c) more than three months prior to the filing of the information disclosure statement.
No extensions of time for filing an information disclosure statement are permitted under §1.136.
In compliance with 37CFR 1.98, please find attached copy of U.S. Patent Application Publication number 20140144161.

BACKGROUND OF THE INVENTION

Field of the Invention

This invention relates to temperature stabilizing cargo compartment manufactured from thermal resistant materials (TRM) including but not limited to vacuum insulated panels (VIP), Polyisocyanurate (also referred to as PIR), or other highly thermal resistant materials, or for a transport container that provides for the transport of various serums, samples, vaccines, and other non-specific perishables, products, or materials wherein it is important to maintain a consistent temperature environment for extended periods of time, wherein the internal air temperature maintains a constancy, or near constancy (depending on the frequency of opening and closing of the compartment itself) if temperatures within an acceptable range; specifically to keep the air cool without freezing the cargo, or keep the air warm without overheating the cargo, as prescribed by the intended use of the cargo packaged at the desired temperature into the temperature stabilizing cargo compartment, (or abbreviated as: "TSCC") of either a cold chain or warm chain container.

One embodiment of this invention discloses an ergonomic container for the transport of various serums, samples, vaccines, and other products or materials wherein it is important to maintain a cool environment in which the proximal side wall is inwardly curved in a contour adapted to an adult human user's body. The opposite or distal side wall may also be curved with a contour that is symmetrical with the proximate side wall or be spared to maximize the cargo space and dividers held therein. The side walls and end walls have an outwardly-turned peripheral top edge forming a lip, the lip being extended downward along at least a portion of the proximal side wall to form a cushion portion. Upward channeled vents are provided along the periphery of the container between the lip and the end walls and side walls other than the cushion portion to allow for reduction of condensation or drainage of melting ice. A centrally located handle grip is molded into the top of the container that snuggly fits over the top of the cargo area but is recessed into the square or rectangle cargo container. The top can be clamped in place and locked with a standard lock placed through a hole molded into the top and clamps that can be affixed to the sides of the container. The container will have molded in slotted handles on the sides of the container whereby adjustable straps can be attached for ease of transport similar to a backpack, or over one shoulder.

One embodiment of this invention discloses a surface modified composing of a surface modifying gas fuming fine particles of resin to be used in manufacturing the surface structure or article, or the completed structure or article, thereby providing certain desired properties including but not limited to binding with various metals, antimicrobial, barrier, hydrophobic, antistatic, etc.

One embodiment of this invention discloses a transport container of any size, for any utility, manufactured by using a priority process of Powder Impression Molding (PIM) and/or Rapid Encapsulation Molding (REM) to make the various components of said transport container.

One embodiment of this invention addresses a method of stabilizing and maintaining the interior air temperature of a cargo compartment of a transport container; and the development of an insert for existing transport containers including but not limited to a uniquely designed cold chain or warm chain container for the transport of various serums, samples, vaccines, and other products or materials, wherein it is important to maintain a cool, or warm, or temperate environment for the preservation, performance, or quality purposes.

BACKGROUND OF INVENTION

Although there have been many attempts to invent a better temperature stabilizing transport container, there has been an apparent deficiency in developing one that satisfies the requirements of the specialized medical transport containers, (often referred to as cold chain containers), or other containers designed to stabilize the temperature of the cargo designated for transport. This problem becomes particularly of urgent concern when it comes to making deliveries of life saving medical supplies, vaccines, etc., in under-developed regions, where most deliveries of medicines are done by bicycle or on foot.

The unique temperature stabilizing cargo compartment for a transport container herein under consideration, is designed so as to have increased temperature resistance regarding the air within the cargo area of the structure for extended periods of time—anywhere from 1 to 150 hours before air temperatures within the cargo area rise above 8.degree. C. where many serums, vaccines, and specimens will degrade in the instance of maintaining a cold chain of custody for said pharmaceuticals.

In an attempt to keep the cargo compartment <8.degree. C. previous inventions found in prior art, have used various refrigerants, dry ice, and cooling devices, but said measures have often resulted in too low of temperatures that can cause the cargo to become frozen, thereby adversely affecting the cargo that the container was designed to protect.

A solution to this problem has evaded prior inventors because of the many variables involved in the cooling and freezing process. Factors determining the time it takes water or other liquids to freeze is highly sensitive to a number of details, such as the shape and size of the container, the shape and size of the refrigeration unit, the gas and impurity content of the water, how the time of freezing is defined, and so on.

It has also been proposed that the liquid cargo experiences the Mpemba effect which may be explained by the fact that the temperature of the fluids becomes non-uniform. As the fluids cool, temperature gradients and convection currents will develop. For most temperatures, the density of liquid decreases as the temperature increases. Over time, as the fluid in the vaccines cool to a given average temperature a phenomenon occurs wherein there is a heat loss that becomes greater the more inhomogenous the temperature distribution is, (that is, the greater the range of the temperatures seen as we go from the top to the bottom). Initially the warmer fluids in the vaccines and serums will cool rapidly because the core temperature is warmer thereby quickly developing convection currents, and so the temperature of the cargo will have greater convection currents, and thus have a faster rate of cooling then the already cold liquid in the coolant such as is found in icepacks.

Another theory is that as thermodynamics equalize the temperature between the cargo and the coolant, the heat loss is absorbed by the air within the container until the air, coolant, and cargo temperature is equalized. Because the mass of the coolant exceeds the mass of the cargo, the cargo heat loss exceeds that of the coolant. The freeze barrier embodiment of this invention obstructs the absorption of heat that is loss from the larger mass—the coolant, by the lower mass—the cargo. The air inside of the container has the least amount of mass and so is the least affected by the loss of heat by either the coolant or the cargo, so stabilizing the air temperature becomes key to stabilizing the temperature of the cargo and the coolant.

The freeze barrier embodiment of this invention provides a superior mass for heat transference without the occurrence of convection because the TRM is most effective if it is a vacuum insulated material whereby there is little or no available free mass to be affected by entropy, thereby establishing a more stable air temperature environment, and consequently a more stable cargo temperature sustained for longer periods inside the temperature stabilizing compartment.

In the absence of a freeze barrier the coolant and the environment, including the cargo soon reach the same temperature. Entropy dictates that the energy will continue to cool the cargo within the container thereby freezing the vaccine rendering a substantial portion of the vaccines worthless, depending on their position in the container and proximity to the coolant. This discovery has led the Center for Disease Control (CDC), to develop new guidelines for handling vaccines and serums delivered by hand-held cold chain containers. The processes cannot conclusively be determined in each instance because the laws of thermodynamics are effected by a host of variables as simple as how often the container is opened, thereby changing the internal temperature of the container and the TSCC. The freeze barrier embodiment of this invention discloses a TRM including but not limited to VIP, PIR or other TRM. The freeze barrier inhibits the heat loss from the air within the TSCC cargo from falling below 0.degree. C. thereby causing the cargo to freeze. In this embodiment, the air temperature is cooled thereby preserving the cargo, but the freeze barrier prevents freezing of the cargo itself.

Transversely, the same thermal resistant properties of the temperature stabilizing cargo compartment can be applied when the desired utility for the cargo compartment is to stabilize the air temperature within the temperature stabilizing cargo compartment at warmer or moderate temperatures. In this embodiment of the invention the TRM prevents heat loss and the heat barrier prevents overheating of the cargo from the heat source.

One embodiment described herein, allows an exception to the freeze barrier requirement of the temperature stabilizing cargo compartment, when the desired result is to keep an already frozen cargo frozen. This exception applies in the instance where the cargo is already frozen and the requirement is to prevent the air temperature inside of the TSCC from rising above 0.degree. C. In this embodiment the TRM serves as a heat barrier only.

One embodiment of the invention maintains the constancy of the air temperature within the temperature stabilizing cargo compartment, and is not directly focused on cooling or warming the cargo itself. The cooling or warming are functions of the coolant or heat source, whereas the focus of this embodiment is the maintenance of the air enclosed in the cavity of the temperature stabilizing cargo compartment, keeping the air at a substantially constant temperature for an extended period of time, with no regard to the method of cooling or warming. This function of a thermal resistant, insulative material would stabilize the interior air environment by limiting a transference of energy between the coolant or heat source, and the air within the temperature stabilizing cargo compartment. The cargo itself would aid in stabilizing the interior air temperature as the cargo would emit a degree of energy that would be contained within the compartment.

The thermal resistant material would also provide a freeze barrier or transversely a heat barrier between the coolant or heat source, depending on the prescribed utility of the transport container.

In the preferred embodiment of this invention the construction of the temperature stabilizing cargo compartment is made from vacuum insulated panel (VIP, PIR, or other TRM) material to provide the necessary thermal resistance for stabilizing the air temperatures within the invention, as well as to serve as an excellent freeze or heat barrier between the cargo and the coolant, or transversely the heat source; thereby preserving used to preserve the cargo for extended periods of time. In this embodiment VIP, PIR, or other TRM is the thermal resistant material used for at least one surface of the temperature stabilizing cargo compartment, however the scope of this invention is not limit to the use of VIP, PIR, or other TRM only, but applies to any thermal resistant material that proves to provide adequate insulative value, and has the integrity to provide a freeze or heat barrier between the cargo and the coolant or heat source respectively.

In one embodiment of this invention, the internal air temperature of the temperature stabilizing cargo compartment constructed from TRM including but not limited to VIP, PIR, or other TRM, is maintained at a constant <8.degree. C. for extended periods of time, by means of utilizing the highly insulative properties of the TRM. In one embodiment VIP, PIR, or other TRM is the preferred TRM as part of the construction of the TSCC, and is used as both an insulator in order to maintain air temperatures, and also as a freeze or heat barrier.

In the embodiment where the TRM is VIP, PIR, or other TRM, the VIP, PIR, or other TRM is encapsulated on at least three sides with a protective sleeve that prevents tearing of the outer membrane of the VIP, PIR, or other TRM material. The vacuum insulated panel (VIP, PIR, or other TRM) is a technologically advanced product that combines high R-value in a relatively thin panel. The vacuum insulated panel consists of a special core panel enclosed in an air-tight envelope, to which a vacuum is applied. This product provides an insulative value of three to seven times that of equivalent thickness of other insulation materials, such as rigid foam boards, foam beads, or fiber glass, or other forms of insulation and/or padding. Panels can be fabricated in virtually any size, making them ideal as the thermal resistant material—TRM as disclosed herein.

The core of the vacuum insulated panel is an open-cell material that allows a vacuum to be pulled on the assembly. There are several types of cores that are currently being used in vacuum insulated panels: polystyrene, polyurethane, and a combination of silica, titania and carbon. The core is wrapped in a metallic or mylar foil, and the vacuum applied. The metallic film is sealed to maintain the vacuum for a long period of time. Seals are very important, as they represent the weak point of the envelope assembly.

Because there may be some loss of insulative value as the panel ages, depending on the design of the installation, the protective sleeve must be tough, yet resistant to moisture, and easily cleaned and sanitized. Desiccants are included in the panels to remove any moisture that may occur in the panel. Special materials known as "getters" are used in the panels to absorb gases that may infiltrate the panels.

In one embodiment of this invention, the TSCC is inserted into various existing transport containers, and is not in any way limited to any size or shape or specific material as part of the construction thereof. The TSCC disclosed herein in a preferred embodiment is applied to a hand-held transport container but is not limited to such. The same invention is embodied in applications that include but are not limited to smaller shipping or hand-held containers, packaging for shipping, hand-held personal containers like cups or lunch bags, delivery containers such as shipping boxes or pizza delivery boxes or bags, or larger, truck size containers or shipping containers are not excluded, and shall apply to any enclosure to the cargo compartment of any transport container as described herein.

In one embodiment of this invention the TSCC for a transport container can be used to maintain warm air in the cargo compartment of the container by utilizing the insulative properties of VIP, PIR, or other TRM or other TRM construction. In this embodiment the internal air temperature of the TSCC can be stabilized to enable the maintenance and stabilization of said air temperature to keep the cargo warm; as in the case of certain gasses, chemicals, isotopes, or certain medical applications wherein the cargo must be kept in an environment at temperature of >8.degree. C. and at the same time not to become too warm so as to degrade the cargo.

One embodiment of the invention, a warming device, or phase change material (PCM), a thermal electric device (TED), or other heat source product, or chemical reaction, or even hot water would be used to warm the interior air of the cargo compartment so as to keep the cargo at the desired temperature, while the TRM would provide thermal resistance to outside temperatures thereby stabilizing the interior air temperature and thereby the cargo contained therein.

In the claims for all embodiments disclosed herein is the inclusion of, but are not limited to the stabilization of the air temperature itself when the cargo compartment is constructed from TRM including but not limited to VIP, PIR, or other TRM, and thereby applying the TRM technology to provide thermal stability and thereby stabilize said interior air temperatures of the cargo compartment when the interior air is exposed to a coolant, or warming device, or when the contents of the cargo compartment are already sufficiently cooled or warmed or at the temperature desired for their ultimate use, and the exterior environment may compromise the temperature of the air space within the cargo compartment described herein; and the dwell time required prior to delivery exceeds one hour and maintain the air within the temperature stabilizing cargo compartment at a substantially constant temperature for an extended period of time.

Also important as part of the claims of this patent application is the existence of a freeze or heat barrier as part of the TSCC. The properties of the TRM prevent the cargo from becoming too cold and freezing, or too warm and overheating as the cargo comes into contact with the conditioned air within the TSCC.

One embodiment of this invention applies to any size, application, or utility of a temperature stabilizing cargo compartment used to stabilize the air temperature in the interior of any said cargo compartment of any transport container in any size or shape, designed for any application or utility of said container, and as an insert that may be placed within any transport container.

Another embodiment of this invention applies to any size, application, or utility of a temperature stabilizing cargo compartment used to stabilize the air temperature in the interior of any said cargo compartment of any transport container in any size or shape, designed to include a freeze barrier or heat barrier made from any thermal resistant material, designed for any application or utility of said container, and as an insert that may be placed within any transport container.

In one embodiment of this invention, any and all vacuum insulated panel walled construction, including said VIP, PIR, or other TRM used in one or more surfaces, for the purpose of stabilizing and maintaining cargo compartment air temperature below temperatures of 8.degree. C., preventing ice melt, and preserving non-specific perishables, or transversely, sustaining adequate warmth above 8.degree. C. within the cargo compartment for certain applications is herein contemplated.

Because the TSCC can be used to transport samples and specimens, and because the container is often in an area where there is a high concentration of contagions, with limited hygienic solutions, one embodiment of the TSCC disclosed herein, is to provide a surface modified material for the interior surface wall and or other surfaces of said TSCC or the entire transport container, thereby conveying certain properties to the material from which the surface is manufactured. This can be done by several means, however for this embodiment a compound of pretreated plastics is used either as a coating or as making up the entire structure. Said composite is exposed in finely granulated form to a surface modifying gas such as sulfur trioxide, or fluorine gas, or other gases, and then exposing the now modified material to an antimicrobial agent such as silver, copper, iodine, zinc, and other chemicals that can now become part of the matrix that the composite material is made from. Another way to gain antimicrobial properties is to treat the entire sheet-stock from which the TSCC is constructed, or the completed, manufactured TSCC to the antimicrobial surface modification treatment described herein.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

For the purpose of this patent application, successful reduction of microorganisms is achieved when the populations of microorganisms are reduced by at least about 0.3 log.sub.10., for example at least about 0.3-1 log.sub.10. In this application, such a population reduction is the minimum acceptable for the processes. Any increased reduction in population of microorganisms is an added benefit that provides higher levels of protection. For example, a 3 log or greater reduction is characteristic of a hard surface sanitizer. For example, a 5 log or greater reduction is characteristic of a food contact sanitizer.

Traditional methods for the transport of various serums, samples, vaccines, and other products or materials wherein it is important to maintain a cool environment has been to place the various serums, samples, vaccines, and other products or materials in a conventional Styrofoam cooler. These coolers can become brittle and lack structural integrity thereby often resulting in the loss of valuable medicines or the compromising of various specimens. Additionally, the square edges and straight lines of containers can make them very uncomfortable and bulky to carry for longer distances and over rough terrain, especially when heavily loaded.

In one embodiment the problem of hard shelled (mettle or ridged plastic) coolers is addressed. Commonly used for the transport of various serums, samples, vaccines, and other products or materials wherein it is important to maintain a cool environment, generally have a rectangular crate-like construction. These containers usually have a hinged top lid that fits securely inside and on top of the container. The handles are usually strips of wire, rope, or plastic, or small cavity in the sides of the container, often having a small diameter or a sharp edge which can cut into or pinch the hand, making them uncomfortable to grip and carry as the containers become filled and heavy.

Most handles do not provide proper balance for carrying a loaded container. The manner in which these handles are attached to the containers, the small diameter of the grip allow the container to pivot and sway when the carrier is walking or biking, which may cause items to shift in the container or spill from it. Fragile items within the container may be damaged if shifting causes impact against a hard surface.

When a container is carried, and particularly if it is permitted to swing because of the handle design, the edges and corners of traditional rectangular containers impact the user's body. Because the length of these handles is largely dictated by the size of the container, these containers often hang low and impact the user's legs in the knee or upper shin area.

When a heavy load is carried in such known containers, a considerable torque is placed on the user's back, elbow and wrist. The orientation of the handles on existing containers tends to twist and lock the user's elbow in an uncomfortable position.

In addition to the problems related to handles, the traditional containers are not ergonomically shaped, generally having straight sides which do not conform to the curve of a user's body. If the container is held close to the body, the straight rigid sides make the containers awkward and uncomfortable to carry and walk with.

Some attempts have been made to address the deficiencies and uncomfortable nature of these containers and user's displeasure with them. Some have fit pieces of tubing, foam, vinyl, etc., over the grip portion in efforts to make the handles less painful to hold. These attempted solutions only slightly increased the diameters of the handles, did little to decrease pinching between the two handles, and completely failed to address the many other problems (such as handle length, shape of the container, point-of-contact with the body, swinging, etc.). Containers with traditional plastic handles also tend to break at the pivot points where the handles connect to the container.

Addressing the Challenges of Conventional Coolers

The challenge addressed by one embodiment of the invention is to design a container that overcomes the problem of insufficient cooling capacity because of ice melt within the cargo area of the container, and at the same time providing a freeze barrier to the cargo compartment when said cargo compartment comes into close proximity to a coolant. Many different types of materials have been explored with some advantages but with many more drawbacks.

Because the desired coolant is ice made from water, (or in some instances frozen gel packs are also acceptable); the inside cargo area rapidly warms to unacceptable temperatures (>8.degree. C.) as the ice melts or the frozen gel packs defrost. Dry ice is not a desirable coolant because it is difficult to manage, unstable and can rapidly freeze the cargo rather than simply keeping it cool, and then as the dry ice dissipates, becomes ineffective as a coolant for the cargo. Other sorbent devices have been used successfully, however these devices are not always approved as a coolant for medical use and in principle these devices are designed to cool the cargo itself, and in some cases, over or under cool the cargo, which can alter the integrity of the cargo rendering it unusable for inoculations or other such medical purposes.

Transport containers are often employed in areas where the climate is tropical, and therefore the outside temperature is hot and sometimes humid; although similar results could be achieved in desert like conditions, or other climate zones. In such an environment, ice from water melts very quickly and frozen gel packs rapidly defrost so as to be of little value in preserving the contents of the cargo area of the container once this happens.

A solution to this challenge is to construct the temperature stabilizing cargo compartment of the transport container utilizing a TRM including but not limited to VIP, PIR, or other TRM for its excelling thermal resistance and available sizing capability. Tests have indicated extended ice from water preservation, as well as resistance to defrost of frozen gel packs, and thereby continued air temperatures within the temperature stabilizing cargo compartment of the transport container to be maintained at <8.degree. C. and >0.degree. C. periods of time lasting as long as 150 hours.

One embodiment indicates that the TSCC maintains even longer cooling capacity using a more stable coolant such as phase change material (PCM), thermal electric devices (TED), and other coolants disclosed hereinafter. Although ice made from water or frozen gel packs are the preferred, other coolants will work as well in extending the cooling environment inside the temperature stabilizing cargo compartment of the container. In this one embodiment of the invention ice from water or frozen gel packs are the principle coolants; however there is no exception taken for dry ice, phase change material (PCM), thermal electric devices (TED), other chemical or electrical or otherwise powered cooling mechanisms that may be suitable for this and other applications for use of the invention and are hereby included as additional embodiments of the invention described herein.

Traditional methods for the transport of various serums, samples, vaccines, and other products or materials wherein it is important to maintain a cool environment, has been to place the various serums, samples, vaccines, and other products or materials in a conventional expanded polystyrene (EPS) cooler. Although these coolers offer some breakage protection and a margin of protection from heat, they perform poorly when compared to vacuum insulated panels. Most EPS containers exhibit an insulation value of R5/inch rating whereas VIP, PIR, or other TRM has an R40/inch rating or even as high as R50/inch in some cases and the preferred TRM for one embodiment of this invention. EPS coolers also have proven to be brittle and often lack structural integrity thereby resulting in the loss of valuable medicines or the compromising of various specimens. Coolers made from polyurethane foam perform better, but fall short of the desired term and constancy requirements for longer delivery times of the cargo to and from the desired destination.

Often the destination of the cargo is in areas where in most cases, the only available coolant is ice made from water or commercially available gel packs. Although ice made from water is not restricted as the only coolant, it is often the one method available. In many cases the US CDC restricts the use of any other coolant except ice made from water, or even cool packs, (cold water in a plastic enclosure), to prevent freezing the cargo. In one embodiment of this invention ice made from water and frozen gel packs can be used interchangeably, depending on the specifications of the consumer, and the manufacture of the cargo.

The use of VIP, PIR, or other TRM as the selected TRM inhibits heat transference either into or out of the temperature stabilizing cargo compartment thereby allowing the designated coolant to extend the time period wherein there is a cooling of the air, or the designated heating source to extend the warming of the air temperature inside the temperature stabilizing cargo compartment, to provide a freeze barrier or heat barrier of a transport container is the basis of one embodiment of this invention.

The vacuum insulated panels discussed in one embodiment of this invention address a core deficiency of other cold chain transport containers of medicines, specimens, and even food products or liquids if desired or necessary . . . specifically, to maintain a consistent temperature environment for extended periods of time, wherein the internal air temperature maintains a constancy of temperatures within an acceptable range as prescribed by the intended use of the cargo placed at the desired temperature into the temperature stabilizing cargo compartment of either a cold chain or warm chain container.

Transversely, the same holds true when it becomes necessary to maintain warmth within acceptable ranges depending on the prescribed use by the application. Essentially, what is claimed is the stabilizing of the interior air of the temperature stabilizing cargo compartment for a transport container.

Because the desired coolants are ice made from water and/or frozen gel packs, the inside cargo is safe from leakage of chemical coolants in the event of an accident. In another embodiment of this invention, said container could be used to transport such perishables as fish, shellfish, meat, poultry, milk, chocolates, or other desired foodstuffs and can be scaled to a much larger transport vessel to allow for volume shipping.

One embodiment of the invention discloses an ergonomic cold or warm chain transport container that satisfies the above-identified needs. A container having features of the present invention includes side-walls having fin-like vents to allow for drainage of melted ice, and to prevent condensation, or a desiccant filled liner for absorption. The proximal side wall (closest to the user's body) is inwardly curved in a contour adapted to an adult human user's body. The opposite or distal side wall may also be curved with a contour that is symmetrical with the proximate side wall. The side walls and end walls have an outwardly-turned peripheral top edge forming a lip, the lip being extended downward along at least a portion of the proximal side wall to form a cushion portion. A double-walled cargo compartment provides an area for holding ice, or some other approved coolant, and the interior walls of the cargo compartment are ribbed so as to provide slots for inserting dividers inside of the cargo compartment. A centrally located handle grip is molded into the lid that has a snap off bottom and a hollow cavity for holding ice, or some other approved coolant. The lid also fits securely inside of the cargo compartment.

The grip handles are open slotted so as to allow for the addition of a strap mechanism for ease in transporting the container over long distances and rough terrain. The preferred aspect of this invention is to construct the entire structure using a patented process known as powder impression molding or PIM™. This process allows for the outer skin to be made from materials having varying properties, and the filler material to have an isolative property.

One embodiment of the invention discloses a transport container of any size or shape manufactured by utilizing certain proprietary technology including but not limited to Powder Impression Molding (PIM), and Rapid Encapsulation Molding (REM) whereby the article or components of the article are constructed of a light-weight structure that can further be made with a surface modified utility surface that would have antimicrobial, antistatic, bonding, hydrophobic, etc. properties as a permanent part of the surface.

Description of Need

There is a need for a cold chain transport container that is can ensure constancy of the cargo compartment air temperature to <8.degree. C.

There is a need for a cold chain transport container constructed from temperature resistant materials including but not limited to VIP, PIR, or other TRM materials, for performance purposes in order to achieve constancy of the cargo compartment air temperature to <8.degree. C.

There is a need for a cold chain transport container constructed from temperature resistant materials including but not limited to VIP, PIR, or other TRM materials, that is able to maximize the cooling properties of ice from water or frozen gel packs to achieve constancy of the cargo compartment air temperature to <8.degree. C. for extended periods of time in the range of 1 to 150 hours inside of the closed cargo area.

There is a need for a cold chain transport container constructed from temperature resistant materials including but not limited to VIP, PIR, or other TRM materials, that is able to preserve ice made from water or gel packs, at a temperature of 0.degree. C. for extended periods of time thereby maximize the cooling properties of ice from water or frozen gel packs to achieve constancy of the cargo compartment air temperature to <8.degree. C. for extended periods of time in the range of 1 to 150 hours inside of the closed cargo area.

There is a need for a warm chain transport container constructed from temperature resistant materials including but not limited to VIP, PIR, or other TRM materials, that is able to maximize the warming properties of a heat source in order to achieve constancy of the cargo compartment air temperature to >8.degree. C. for extended periods of time in the range of 1 to 150 hours inside of the closed cargo area.

There is a need for a cold chain transport container constructed from temperature resistant materials including but not limited to VIP, PIR, or other TRM materials, that includes a freeze barrier that would protect the cargo from reaching temperatures reaching 0.degree. C., while not inhibiting the maximum cooling properties of ice from water or frozen gel packs, or other cooling methods, to achieve constancy of the cargo compartment air temperature to <8.degree. C. for extended periods of time in the range of 1 to 150 hours inside of the closed cargo area.

There is a need for a warm chain transport container constructed from temperature resistant materials including but not limited to VIP, PIR, or other TRM materials, that includes a heat barrier that would protect the cargo from overheating, while not inhibiting the maximum warming properties of heat source, to achieve constancy of the cargo compartment air temperature to >8.degree. C. for extended periods of time in the range of 1 to 150 hours inside of the closed cargo area. These needs listed above herein may be satisfied by a novel container of the present invention.

There is a need for a cold or warm chain transport container that is constructed in such a way as to provide two smooth exterior finishes, and a filler material that does not easily allow for the transfer of heat from the outside ambient temperature, to the cargo area, nor cold from the cargo area to the outside surface of the container, thus better preserving the contents, and not causing discomfort to the individual transporting the container when coming in contact with the human body.

There is a need for a cold or warm chain transport container that demonstrates antimicrobial properties, as well as antistatic, hydrophobic, and bondability to other materials when constructed from a surface modified material.

DESCRIPTION OF RELATED ART

Various approaches have been taken by the art to address some of the foregoing issues of shipping objects, and have obtained varying results. For example, Karow, U.S. Pat. No. 4,262,494, discloses a system of three containers for the freezing and short-term storage of semen, and other similar tissues, at low cryogenic temperatures after collection and during conventional transportation to a permanent storage facility. According to Karow, tissue straws or tubes, containing the treated tissue, are secured inside a hollow canister of heat conducting material in such a way as to prevent the straws from being in contact with the interior walls of the canister. The canister is then filled with an insulating medium and is secured in an insulated metal box, and the insulated box is surrounded on all sides with a solid freezing medium in a shipping container. The insulating medium in the canister and the insulation of the box are said to be selected for quality and quantity to attain the desired rate of temperature change, but should be of a gas (e.g. air) or liquid which does not change physical form (liquify or freeze) in the temperature range to which it will be subjected and which does not chemically interact with the invention components, including the semen straws. The straws must be secured within the canister in a manner to prevent them from being in contact with any heat conducting materials other than the insulating medium. The insulating medium surrounding the straws, as cooled by the canister walls, is said to provide the controlled-rate of cooling and freezing for the tissue. By varying the quantity and quality of the insulating medium the rate can itself be varied.

Foster et al., U.S. Pat. No. 5,417,082, discloses an insulated container which uses two coolants at different temperatures, such as ice water and dry ice, respectively, disposed on opposite sides of an object. The object is separated from both refrigerants by heat regulators of an insulating material of different thicknesses. It is said that the thicknesses of the insulating material can be varied such that the object is maintained at a specific temperature along a temperature gradient existing between the temperatures of the two coolants. The object may be disposed within a thermally conductive box which maintains a uniform temperature throughout the product. Foster also discloses a shipping container which is said to be able to maintain an object at a constant user-selected temperature within a specified range of temperatures for maintaining a uniform temperature throughout the product. According to Foster, the shipping container may be of a reduced weight which maintains the product at the specified constant temperature for an extended period of time.

Bane III, U.S. Pat. No. 5,441,170, discloses a reusable insulated shipping container which is said to be made of sturdy, lightweight insulated panels, and which is said to be adapted for transporting multiple uniquely temperature sensitive objects in one overall container, over extended time periods, without the need for elaborate temperature control systems. According to Bane, the container is said to isolate each object transported, such that the temperature of each object remains virtually unaffected by the temperature of the other objects being transported. The container may include removable multiple insulated inner containers formed from a plurality of rigid foam panels, and a removable spill containment device, such as a liner, which prevents leakage of liquids and provides additional protective padding. It is also stated that the container allows for shipping a non-temperature sensitive object together with a temperature sensitive object, without affecting the quality of each object.

Meyer et al., U.S. Pat. No. 5,827,385, discloses an evacuated insulation panel or container which may be used for forming an insulated shipping container, and a method of producing the insulated panel or container. According to Meyer, an insulated panel or container also allows for efficiently producing containers with a minimum wall thickness and with a minimum heat transfer. According to Meyer, the evacuated insulation panel or container may be formed in practically any shape and may be rapidly evacuated for obtaining high volume production. In one embodiment, an evacuated insulated container is formed by a pair of opposing and identical insulated panels each of which includes a vacuum formed semi-rigid sheet of gas impermeable plastics material forming a tray or shell having a bottom wall and side walls defining an open top cavity, and the side walls extend to form an outwardly projecting peripheral planar flange. The cavity is filled with an insulation media or material such as silica powder or rigid open cell foam, and a sheet of porous filter material may be placed over the filled cavity and sealed to the flange to hold the powder within the cavity during evacuation. The shell with the insulation is then placed within an evacuation chamber which encloses a platen positioned above the tray, and the platen may be heated. A sheet of gas impermeable plastics material is supported between the platen and the peripheral flange of the shell. After air is evacuated from the insulation media, the cover sheet is pressed and sealed against the peripheral flange by welding or adhesive to form an air-tight sealed cavity enclosing the insulation media. Each shell is provided with inner and outer lip portions on opposite side walls of the shell and with a partial crossover recess, so that two of the insulated panels may be pressed together to form an insulated container defining a chamber for receiving a temperature controlling media such as dry ice and a temperature sensitive article such as a pharmaceutical drug.

Grabowski, U.S. Pat. No. 5,956,968, discloses a cold pack for medicinal vials which includes an outer housing attached to a base, wherein the base has a supporting depression therein for receiving a tray of medicinal vials. The outer housing has a hollow interior for receiving the tray therein. The tray is enclosed by a closure means keeping the tray in a chilled state inside the housing. To further the cooling ability of the cold pack for medicinal vials, the cold pack may be placed within a reclosable insulated bag. The insulated bag can be attached to or placed in the drug case used by medical personnel to transport medicines to the patient's location.

Bane III, U.S. Pat. No. 5,979,693, discloses a reusable insulating panel that can be used in a shipping container to allow temperature sensitive materials to be transported over an extended period of time without the need for external temperature control. The panel is said to separate material being shipped from the exterior shipping container to protect the cargo from objects that may puncture the shipping container, and also provides structural integrity to the shipping container as well as impact protection for the material being shipped. The insulating plate member may be used to separate air compartments, which are co-extensive with the face of the plate member so that convection is not allowed between the compartments.

Miller, U.S. Pat. No. 6,875,486, discloses a packaging system that is said to allow the shipment of objects under low temperature conditions for periods of time of up to 80 hours while effectively maintaining the low temperature conditions and thereby guaranteeing the integrity, wholesomeness and officiousness of the products being shipped. Miller discloses a package construction that utilizes two or more radiant barriers separated in the packaging by a container in combination with suitable insulation. Within the inner radiant barrier is contained two or more phase change materials which are said to change phase at different temperatures. The outer radiant barrier covers the exterior of the packaging. The packaging system is characterized wherein the first phase change material has a phase change at minus 20 degrees centigrade, and wherein the second phase change material has a phase change at zero degrees centigrade. The phase change materials may be in the form of gel packs. The container is a rigid construction made of corrugated cardboard with its exterior completely covered with the first radiant barrier in the form of a film bonded to the cardboard. The insulator is preferably plastic foam. The packaging system has the second radiant barrier in the form of a flexible container, such as a bag or pouch, comprised of an outer laminate of radiant barrier material and an inner laminate of plastic durable at low temperatures.

Gano III et al., U.S. Pat. No. 6,886,357, discloses a container for storing an item that includes an insulating material defining an interior, the insulating material having a bio-based polyurethane; and a temperature-maintaining material disposed within the interior, the temperature-maintaining material being arranged to maintain a temperature of an item placed with the interior.

Smith et al., U.S. Pat. No. 6,968,711, discloses sorption cooling devices and temperature-controlled containers incorporating sorption cooling devices, particularly temperature-controlled shipping containers for the transportation of temperature sensitive products. The sorption cooling device is said to include a liquid supply apparatus that is responsive to changes in the ambient temperature. The apparatus includes a rigid housing, a first flexible pouch disposed within the rigid housing that contains a high vapor pressure substance, a second flexible pouch enclosing a supply liquid and disposed within the rigid housing adjacent to the first flexible pouch and a liquid conduit for providing liquid communication between the second pouch and an evaporator. The high vapor pressure substance causes the first flexible pouch to exert pressure on the second flexible pouch and assist in the flow of liquid from second flexible pouch to the liquid conduit. Increases in temperature increase the vapor pressure within the first flexible pouch, thereby increasing the flow rate of the liquid and the cooling rate.

Merril, Ezra, U.S. Pat. No. 6,838,146 Vacuum thermal insulation product and method for making same which discloses a container made from a vacuum thermal insulation product is formed of aporous thermal insulation material encased in an evacuated enclosure, with least a portion of the evacuated enclosure including a layer of an electroplated metal.

Derfield, U.S. Pat. No. 7,028,504, discloses containers for shipping temperature sensitive products in a refrigerated and/or frozen condition for an extended period of time. The containers may be constructed of, for example, rigid polyurethane foam for, among other purposes, small and large shipments, such as via air freight, including via LD3 shipping containers. The containers are formed of a bottom, preferably with a tray for holding product, four sides, and a lid, and preferably with a coolant tray. The bottom, sides and lid are designed to interlock (the sides and base preferably are slide locked or are tongue and grooved, as versus typical 45 degree corners that do not lock together or "grip" together), so as to reduce thermal convection. The coolant tray is a slide-in tray which contains a suitable coolant such as dry ice or gel packs, and which also is made of rigid polyurethane foam and to maintain the coolant out of direct contact with the product. The interior walls and bottom of the container can be configured to provide a convection design to create a controlled air flow within the product compartment, and this air flow can reduce the temperature gradient within the product compartment and thus provide better and even temperature control when shipping biological and other products. Each of the foregoing documents is incorporated herein by reference in its entirety and for all purposes as if set forth fully again.

As will be appreciated from the foregoing, various attempts have been made to address many of the issues encountered in designing containers and methods for transporting objects and have produced varying results. A problem remains in cases where a product to be shipped must be maintained at a constant temperature range, such as about room temperature. When coolants are placed into containers and various forms of packages, quite often the coolant decreases the temperature of the product to be shipped below the desired temperature range. If, on the other hand, the coolant is not included in the package in the proper amount, the product to be transported may acquire a temperature above the desired temperature range during transport. In either event, shipping products at temperatures outside of optimal ranges will often result in deleterious effects being imparted to the products and, in particular, possible hazards to recipients who are requesting and relying upon health care products.

James, Lizymol Jan. 26, 1999 U.S. Pat. No. 5,863,507: Benchtop Cooler

In this issued patent the inventor claims an apparatus that holds a laboratory tubes and can be kept cool in case of power failure. Although James calls for a cavity that hold multiple tubes, it is specific in requiring a cooling element that actually cools the tubes, whereas the subject of the current application submitted hereto, calls for the sustaining of cooler air and not active cooling of the specimens or tubes themselves. Additionally, James calls for a power cooling element, whereas this invention although not disqualifying the use of a power cooling element, provides for the primary coolant to be ice made from water or frozen gel packs for the stabilizing of the air temperature within a temperature stabilizing cargo compartment.

Garcia, et al. Mar. 18, 2003 U.S. Pat. No. 6,533,031: Method for thermal management of a battery in an outdoor equipment cabinet provides for a cooling pad and a container, along with but as in the case of James above, a power source for cooling the battery is required, and does not specifically address cooling of or keeping cool of the air within the apparatus.

Eller, Jun. 17, 2007, Dec. 18, 2008, US Patent Application 20080308452: Containers for transferring products and methods for their transfer provides for methods, systems, and containers for transporting products, such as medical products are disclosed. The methods and systems involve identifying an environmental condition of a place to where a product is to be shipped, identifying an environmental condition of a place from which the product is to be shipped, identifying the amount of time that the product is expected to be in transit during shipping, and determining the type of container and cooling element that should be employed to transport the product. Although Eller's application does discuss the maintaining of the cool air in his invention, he does not specify any particular system to achieve this objective, but instead claims a system that identifies the various containers needed for the transport of various materials.

The patents searched in the published literature and referenced herein include cooling the cargo rather than cooling or maintaining cooler air within the cargo compartment thereof or in the case of Eller, a system for deciding which type of container to use in order to maintain the desired environment required for the cargo. Additionally, none of the patents searched in the published literature and listed herein describe a temperature stabilizing cargo compartment that can be inserted into existing transport containers.

Although many basic ice/EPS systems are in use, there is a wide variation in quality and performance of the packaging depending on the value of the product and the sensitivity of the product to temperature fluctuation. A relatively simple system includes a cardboard box into which EPS sheets have been cut and placed. The container is then filled with dry ice in which, for example, frozen fish is shipped. A more sophisticated approach is a validated system consisting of custom molded EPS forms in a rigid box with both frozen and warm gel packs, the combination of which has been tested through a range of temperature cycles for specified thermal properties. Such a validated system can be used for shipping pharmaceuticals. For example, many pharmaceutical products such as vaccines and antibodies must be maintained within a range of 2.degree. C. to 8.degree. C.

The existing ice/EPS cooling system is unsatisfactory for various reasons including: increased environmental concerns associated with the disposal of large quantities of EPS and gel packs; the high cost of shipping; and the required freezers at the shipping source to maintain the frozen packs. The high cost of shipping is directly related to the high volume associated with the EPS and the high volume and mass associated with the gel packs. For a one cubic foot box with a 60 hour lifetime at 2.degree. C. to 8.degree. C., over 90 percent of the volume is consumed by EPS and gel packs.

An example of the foregoing system is illustrated in U.S. Pat. No. 5,924,302 by Derifield issued on Jul. 20, 1999. This patent illustrates a shipping container that includes a plurality of cavities adapted to receive a coolant (e.g., gel packs) that surround a cavity adapted to receive an item to be shipped.

Electrically cooled shipping containers are illustrated in U.S. Pat. No. 6,192,703 by Salyer et al., issued on Feb. 27, 2001. This patent discloses a portable refrigerator unit and storage container employing vacuum insulation panels and a phase change material. Phase change materials undergo a change in physical form (e.g., solid to liquid) thereby absorbing heat from the surrounding environment. A battery driven refrigeration system provides cooling of the shipping container.

The use of reactor-based rechargeable portable coolers are illustrated in U.S. Pat. No. 5,186,020 by Rockenfeller et al., issued on Feb. 16, 1993. This patent discloses a portable cooler utilizing a gas-liquid-gas phase change to effect cooling of chamber. However, the reactor-based apparatus disclosed by Rockenfeller et al. requires a source of electricity to effect the initial gas-liquid phase change. As a result, the apparatus occupies additional space and has additional weight, making it cost-ineffective and severely impairing its utility either for a single-use basis or for a shipping container.

A sorption cooler is illustrated in U.S. Pat. No. 5,048,301 by Sabin et al. This patent discloses a sorption cooling unit where the cooling liquid is maintained in the evaporator prior to the sorption process. A disadvantage of this device is that too much energy is consumed by having to cool the cooling liquid in the evaporator upon activation of the sorption unit. Space is also wasted in that the evaporator will require a relatively large volume to enable an efficient evaporation process because both the liquid and evaporation volume are located in the same general space. Furthermore, space limitations restrict the amount of cooling liquid that may be maintained in the evaporator.

Thus, there is a need for a temperature-stabilizing cargo compartment container, such as a shipping container, having a lightweight cooling device that does not occupy a large volume. It would also be advantageous if the temperature of the container was controllable over a range of temperatures. It would also be advantageous if the cooling device had the ability to maintain the reduced temperature for an extended period of time. It would also be advantageous if the cooling device could be used cost effectively on a single-use basis; however if such a device could be made to be cost effectively recycled, it would have a more beneficial effect on the environment as a whole.

BRIEF SUMMARY OF THE INVENTION

In one embodiment of this invention the thermal resistant materials are vacuum insulated panels that are used to maintain air temperatures of <8.degree. C. and >0.degree. C. inside of a cargo containment area of a cold chain transport container, for an extended period of time (1 to 150 hours) using ice made from water or frozen gel packs as the principle coolants, (although this invention does not exclude the use of other coolants or cooling mechanisms). This is accomplished by means of enclosing an air space, creating a cavity in the center, with a floor and lid with at least one wall, floor or lid being constructed from thermal resistant materials including but not limited to VIP, PIR, or other TRM.

In this embodiment, a suitable thermal resistant material including but not limited to vacuum insulation panels are the construction material for said walls, floor, and in some instances, the lid, exposed to the interior cargo chamber, protected by an impermeable sleeve made from plastic, metal, enamel, or any other impermeable, water resistant materials; and having the exterior surface of the walls of each panel protected by an impermeable sleeve made from plastic, metal, enamel, or any other impermeable, water resistant materials; placed within close proximity to a coolant or heat source respectively.

Additionally, an outer shell constructed from corrugated cardboard materials customarily used for shipping or mailing purposes can also be used in some applications for the invention. The TSCC and coolant or heat source are surrounded by a shell and/or padding, structural foam, of another material, albeit metallic, plastics, fiberglass, wood, cardboard, steel or any other material suitable for said construction of a cold or warm chain transport container.

Said temperature stabilizing cargo compartment can then be used as an insert into existing transport containers as a retrofit; or may be introduced as an insert into an entirely new transport container designed for durability and/or comfort.

In the event that the design requirements for the temperature stabilizing cargo compartment call for only one wall, floor, or lid to be constructed from VIP, PIR, or other TRM, a diminished performance may be acceptable and can be anticipated, however tests indicate an improved performance over other insulative materials, even with one surface being made from VIP, PIR, or other TRM. If the cargo only requires an improvement of temperature stabilizing performance over EPS, urethane, fiberglass, metal, or other materials, then VIP, PIR, or other TRM has proven to provide said improvement and therefore one or more surfaces made from VIP, PIR, or other TRM would be included in the embodiment of this invention. This would include any TRM being wrapped around the cargo to form a cargo compartment that is cylindrical in shape, and thereby forms a TSCC and freeze or heat barrier for said cargo.

One embodiment of this invention is the disclosing of a freeze or heat barrier between the coolant or heat source and the cargo itself Said temperature stabilizing cargo compartment discloses said freeze or heat barrier made from a thermal resistant material (TRM) including but not limited to VIP, PIR, or other TRM, and would include any size or shape of the aforementioned barrier.

The cavity comprising the temperature stabilizing cargo compartment of the container made from any thermal resistant material including but not limited to any vacuum insulated panel having been formed by means of thermal insulation consisting of a nearly gas-tight enclosure surrounding a rigid core, from which the air has been evacuated. By removing air from fiber, powder, or foam core materials VIP, PIR, or other TRM's achieve high thermal performance at a fraction of the thickness of cut-to-fit, or foam-in-place insulation materials.

In one embodiment of this invention the VIP, PIR, or other TRM is invented by Smith et al. included herein by reference, and is a patented formulation for thermal insulation of a porous solid that is several processes which yield both low density and small pores. Its chemical composition is silica, titania and/or carbon in a 3-D, highly branched network of primary particles (2-20 nm) which aggregate into larger (nm to mm) particles The material has pore sizes ranging from 10-100 nm. It is this nano-scale porosity that gives VIP, PIR, or other TRM its excellent thermal performance.

A VIP, PIR, or other TRM constructed cargo compartment for one embodiment of this invention, uses the insulating effects of a vacuum to produce much higher thermal resistance than conventional insulations described in prior art and currently available to the public. Conventional insulation produces an R-value of five or less per inch (fiberglass being towards the lower end and foam panels towards the higher end). VIP, PIR, or other TRMs are commonly as high as R-30 per inch, and have achieved commercially viable levels of R-50 per inch.

In one embodiment of this invention, the VIP, PIR, or other TRMs consist of:
Membrane walls, used to prevent air from getting into the vacuum area
Core material, used to hold the vacuum inside the membrane while preventing the membrane walls from collapsing. (e.g. fumed silica, aerogel, glass fibers or foams)
Chemicals to collect gases leaked through the membrane or off-gassed from the membrane materials are added to VIP, PIR, or other TRM with glass fibers or foams cores, as core with bigger pore size requires vacuum level lower than about 1 mbar during the planned service life.

The vacuum, (or near-vacuum), inside VIP, PIR, or other TRM's greatly reduces conduction and convection of heat. This allows for the cargo compartment air and thereby the cargo itself within the cargo compartment, to remain cool via the exposure on the exterior surface of the temperature stabilizing cargo compartment to ice made from water or frozen gel packs, or other coolants, and further, the subsequently chilled air that comes into proximity with the ice made from water or frozen gel packs, and/or other coolants, depending on the specifications and requirements of the materials being shipped.

The same barrier principle would hold true for air exposed to a heat source in that the thermal resistance of the VIP, PIR, or other TRM would act as an insulator to the already heated air or cargo inside of the compartment. Another determining factor is the environment of both the journey and the ultimate destination of the material being transported.

In one embodiment of this invention, the temperature stabilizing cargo compartment is constructed in such a way that it allows for a measure of air to circulate around the contents, further preserving the contents by means of cold air that has been cooled by the ice contained in the coolant compartments, frozen gel packs, or the loose ice, or other coolants distributed throughout the cargo area.

Transversely, the temperature stabilizing cargo compartment is constructed in such a way that it allows for a measure of air to circulate around the contents, further preserving the contents by means of air that has been heated by a heating element, chemical reaction, or hot water or hot stones in some application.

Also included in one embodiment of this invention is the capacity to insert the disclosed cargo compartment into any existing transport container so as to retrofit said existing transport container into an improved cargo carrier by conveying the attributes of this invention to already existing transport containers already in use or approved for use for various applications and utility thereof.

In one embodiment of this invention, the TRM construction includes but is not limited to VIP, PIR, or other TRM, for the temperature stabilizing cargo compartment making up the interior cargo compartment walls, has the capacity to inhibit the elevation of the interior cargo compartment's temperature that has been cooled with ice made from water or frozen gel packs, from rising above 8.degree. C. for when the cargo is already at a stable temperature of 8.degree. C., for a period of time no less than 1 hour, with tests indicating a possible cool maintenance period of up to 150 hours or more, depending on exterior temperatures and starting temperature of the cargo itself.

One embodiment discloses an ergonomic container for the transport of various serums, samples, vaccines, and other products or materials wherein it is important to maintain a cool environment in which the proximal side wall is inwardly curved in a contour adapted to an adult human user's body. The opposite or distal side wall may also be curved with a contour that is symmetrical with the proximate side wall or be spared to maximize the cargo space and dividers held therein. The side walls and end walls have an outwardly-turned peripheral top edge forming a lip, the lip being extended downward along at least a portion of the proximal side wall to form a cushion portion. Upward channeled vents are provided along the periphery of the container between the lip and the end walls and side walls other than the cushion portion to allow for reduction of condensation or drainage of melting ice. A centrally located handle grip is molded into the top of the container that snuggly fits over the top of the cargo area but is recessed into the square or rectangle cargo container. The top can be clamped in place and locked with a standard lock placed through a hole molded into the top and clamps that can be affixed to the sides of the container. The container will have molded in slotted handles on the sides of the container whereby adjustable straps can be attached for ease of transport similar to a backpack, or over one shoulder.

Disclosed in this embodiment of the invention discloses an ergonomic cold or warm chain transport container that satisfies the above-identified needs. A container having features of the present invention includes side walls having fin-like vents to allow for drainage of melted ice, and to prevent condensation. The proximal side wall (closest to the user's body) is inwardly curved in a contour adapted to an adult human user's body.

The opposite or distal side wall may also be curved with a contour that is symmetrical with the proximate side wall. The side walls and end walls have an outwardly-turned peripheral top edge forming a lip, the lip being extended downward along at least a portion of the proximal side wall to form a cushion portion. A double-walled cargo compartment provides an area for holding ice, or some other approved coolant, and the interior walls of the cargo compartment are ribbed so as to provide slots for inserting dividers inside of the cargo compartment.

A vacuum insulated panel or other thermal resistant material is disclosed as the barrier layer to prevent freezing melting of the ice, defrosting of other coolants, and temperature stabilization of the cargo therein. Transversely said TSCC prevents loss of heat in the case of a warm chain container. A centrally located handle grip can be molded into the lid that has a snap off bottom and a hollow cavity for holding ice, or some other approved coolant. The lid also fits securely inside of the cargo compartment.

The grip handles are open slotted so as to allow for the addition of a strap mechanism for ease in transporting the container over long distances and rough terrain. The preferred aspect of this invention is to construct the entire structure using a patented process known as powder impression molding or PIM™. This process allows for the outer skin to be made from materials having varying properties, and the filler material to have an isolative property.

One embodiment of the invention discloses a transport container of any size or shape manufactured by utilizing certain proprietary technology including but not limited to Powder Impression Molding (PIM), and Rapid Encapsulation Molding (REM) whereby the article or components of the article are constructed of a light-weight structure that can further be made with a surface modified utility surface that would have antimicrobial, antistatic, bonding, hydrophobic, etc. properties as a permanent part of the surface.

One embodiment of this invention is the construction of a temperature stabilizing cargo compartment constructed from thermal resistant materials including but not limited to vacuum insulation panels, having the properties of preserving a cargo compartment interior air temperature <8.degree. C. and >0.degree. C., making up at least one or more surfaces including walls, floor and lid. Said temperature stabilizing cargo compartment constructed from VIP, PIR, or other TRM is designed to maintain constant air temperatures necessary to preserve medicines, vaccines, serums, specimens, tissue, organs, as well as any other non-specific perishables whereby the perishable transported in said container must be transported at temperatures <8.degree. C. for at least one or more hours.

In another transverse embodiment of this invention said temperature stabilizing cargo compartment constructed from thermal resistant materials including but not limited to vacuum insulation panels, having the properties of preserving a cargo compartment interior air temperature >8.degree. C., for a prescribed cargo to be >8.degree. C. for at least one or more hours.

In all embodiments of this invention for a temperature stabilizing cargo compartment are constructed from thermal resistant materials including but not limited to vacuum insulation panels, having the properties of preserving a cargo compartment interior air temperature <8.degree. C. and >0.degree. C., making up at least one or more surfaces including walls, floor, and lid; the thermal resistant properties of the VIP, PIR, or other TRM in extending the desired air temperature within the temperature stabilizing cargo compartment to either <8.degree. C. or >8.degree. C. for at least one or more hours with the potential to exceed 150 hours of sustained air temperature within the cargo compartment thereby sustaining the integrity of the cargo.

Referring to the drawings, wherein like numerals refer to like elements, the present invention generally comprises an ergonomic cold or warm chain transport container, contoured to the shape of an average adult human user's natural body curve and having centrally located handles cut into the sides of the container. The container is preferably constructed of thermo-plastic material by powder impression molding (PIM™) process or rapid encapsulation molding (REM™).

The proximal side wall curves inwardly towards the center of the container in a contour adapted to the shape of an adult user's natural body curve, so the container can be held comfortably against the user's body. As used in this description and the claims, the term curved is intended to encompass a smooth curvature such as shown in the drawings, and also to encompass an effective curvature which can be obtained by straight surfaces angled inward toward the longitudinal axis of the container. When the container is carried by a user with the curved proximal side wall facing the side of the user's body, such orientation shifts the center of gravity of the load closer to the user, and spreads the point of contact with the user's body over a larger surface area than contact with a straight side wall. The curvature is adapted to an adult user's natural body curve in the sense that the container will normally be across the mid to lower back or along the side of the body at the mid-section, or sometimes near the mid-thigh area, and must accommodate fore and aft movement of the thigh during walking. The container can also be held against the torso along the upper hip area using the alternative finger grip described below. These considerations usually result in a relatively long and shallow curvature. Because the container is often carried on the back of a courier riding a bicycle, or carried long distances on foot, the container is also equipped with a carrying strap that is threaded through loops molded into the container mid-section.

The side walls and distal walls have an outwardly-turned peripheral top edge to form a lip or rim. In one embodiment of the present invention, as shown in FIG. 23, the lip is extended further downward along the proximal side wall to form a cushion portion to further spread the point of contact and make the contact against a yielding surface.

The distal side wall may be straight, or also be curved inward, but in the depicted embodiment the distal side wall is curved outward away from the longitudinal axis of the container. In a preferred embodiment, the distal side wall has an outward curvature substantially symmetrical to the inward curvature of the proximal side wall. The lip on the distal side wall may have a short center extension wherein the lip is extended outward along a center section of the distal side wall to form a cushion and a finger grip. The finger grip function allows the user an alternative means to grasp the container, usually while pressing the proximal side wall against the torso.

The container side walls and the distal wall may be provided with closable ventilation slots as shown in FIG. 13, to assist in prevent condensation, and to allow melted ice to drain from the coolant cavity.

Two sides of the lid of the container are molded with finger-grip handles and are flush with the top surface of the lid covering the TSCC cavity. The side handle grips are also flush with the side walls and have an opening below the in the cup of the handle where a strap mechanism can be used for easier transportation of the container.

One embodiment of the invention discloses the container may be made utilizing the powder impression molding PIM™ process in a two-piece mold thermo-plastic construction. In this embodiment at least one heated mold with a powdered resin applied to said mold until said resin; said resin coated mold then sandwiched as it were, to at least one other heated mold with similarly coated resin deposit; having a heat activated foam core, and may include but not exclusively, a ridged reinforcement material placed within the mold as filler material. Said reinforcement material can be, but is not limited to various other types of foam, steel, aluminum, magnesium bamboo, wood, metal, other rigid plastics, glass, fiberglass, rubber, straw, newspaper, cardboard, corrugated or honeycomb reinforcement structure, plasticized material, regrind plastic, stone, concrete, carbon fiber composites, carbon fiber constructions, Kevlar, and/or other recyclable materials. The entire container may made with a resin that has been treated with a proprietary bonding process including but not limited to MMT, and may be wrapped in a cushioning layer of foam that would now adhere to the adhesive applied to the polymer, and then said cushioning layer could be coated with a protective polymer coating such as polyuria, polyurethane, etc.

One embodiment of the invention discloses at least one structure made from but not limited to material can be, but is not limited to various other types of foam, steel, aluminum, magnesium bamboo, wood, metal, other rigid plastics, glass, fiberglass, rubber, straw, newspaper, cardboard, corrugated or honeycomb reinforcement structure, plasticized material, regrind plastic, stone, concrete, carbon fiber composites, carbon fiber constructions, Kevlar and/or other recyclable materials, and/or (p) Foam Insert composite, and placing said article inside of controlled chamber, wherein the article is encapsulated with an outer skin that air-hardens and provides a ridged protective surface, that can also be a soft (as in the case of a polyuria or polyurethane encapsulant) outer skin depending on the utility of the transport container.

Any surface of any embodiment of the invention disclosed herein may be, but is not limited to constructing a transport container or TSCC with materials that have been surface modified using a Molecular Metamorphosis Technology (MMT) whereby the resin is first exposed in a fuming chamber that may be, but is not limited to a fluidized bed apparatus, along with a specifically measured dwell time and concentration level of a surface modifying gas including but not limited to sulfur trioxide, that is used to provide a treated surface to the resin that can be anywhere from 0 to 50 microns each beneath the exposed surface of the material, and then once the material is neutralized, exposed to various antimicrobial agents including but not limited to silver, copper, zinc, and other antimicrobial chemical agents that become a permanent part of the matrix of the material's surface. This embodiment includes exposing the finished article to said fuming gases in a controlled environment including but not limited to a sealed treatment chamber. This embodiment will provide certain properties to the surface of the articles such as antimicrobial, antistatic, hydrophobic, bondability, and even provide a barrier when desired.

Any embodiment of any container as described herein, including but not limited to the embodiment of an ergonomically designed transport container, a "Pack in the Box™", and any other TSCC application of the embodiments disclosed herein, may include but not exclusively, a surface modification process to be incorporated into the static surfaces of the container or TSCC as disclosed herein.

The present invention may be embodied in other specific forms without departing from the spirit or essential attributes thereof and, accordingly, reference should be made to the appended claims, rather than to the foregoing specification, as indicating the scope of the invention.

EXPERIMENT

Example 1

On Monday Sep. 12, 2011 at 10:00 A.M. an 8 ounce specimen of cool tap water was sealed in a zip-lock baggie to simulate the vaccine that would be transported by a cold chain container. The sample was placed inside of the temperature stabilizing cargo compartment along with a thermometer. The starting temperature of water was measured by a Celsius thermometer prior to sealing the baggie, and determined to be 4.4.degree. C., (about 40.degree. F.). The outside ambient air temperature was kept at a constant 27.degree. C., (about 80.degree. F.). The starting inside air temperature of the temperature stabilizing cargo compartment was also 27.degree. C., (about 80.degree. F.). The temperature stabilizing cargo compartment was made with ½ inch VIP, PIR, or other TRM wrapped around a cavity with a 4".times.4" square of VIP, PIR, or other TRM used as the floor of the compartment, thereby using VIP, PIR, or other TRM for five surfaces. The entire temperature stabilizing cargo compartment was placed in the center of a 1-liter hard plastic cold chain container that is typically used in the field for vaccine delivery. The starting inside air temperature of the cold chain container was 27.degree. C., (about 80.degree. F.). Frozen icepacks were placed next to the VIP, PIR, or other TRM on the outer surface of the VIP, PIR, or other TRM forming an open-ended square around the temperature stabilizing cargo compartment on four sides. The top of the cold chain container was then closed and left alone for one hour. The sample temperature and the ambient air temperature was checked at regular intervals with readings as follows:
TABLE-US-00001 Cargo Time of Area Ambient Date Day Hours Temp. C. Temp. C. Sep. 12, 2011 10:00 AM Start 4.4 27 Sep. 12, 2011 11:00 AM 1 3.9 27 Sep. 12, 2011 12:00 PM 2 3.9 27 Sep. 12, 2011 1:00 PM 3 3.9 27 Sep. 12, 2011 2:00 PM 4 3.9 27 Sep. 12, 2011 11:00 PM 13 2.2 27 Sep. 12, 2011 12:00 AM 14 2.2 27 Sep. 13, 2011 8:00 AM 22 2.2 27 Sep. 14, 2011 10:00 AM 48 2.8 27 Sep. 15, 2011 9:00 AM 71 2.8 27 Sep. 16, 2011 9:00 PM 95 4.4 27

Observations: As the interior air inside the temperature stabilizing cargo compartment came into proximity to the coolant, the air temperature was gradually reduced inside of the compartment. The air temperature inside the cargo compartment stabilized during the first hour. The exact time needed in order to stabilize the air in every scenario is unknown, as the compartment was not opened until 1 hour after the start of the experiment. Once the air temperature stabilized at 3.9.degree. C., the temperature of the water inside air temperature in the cargo compartment was gradually reduced to 2.2.degree. C., thereby gradually reducing the temperature of the water inside of the baggie to a low of 2.2.degree. C., which is within the acceptable range for liquids stored within the compartment. No evidence of ice was observed inside the baggie at any time during the experiment. After 95 hours the water gradually returned to the original temperature of 4.4.degree. C.

Conclusions: A temperature stabilizing cargo compartment can provide an enduring cool environment (<8.degree. C.) for at least 95 hours. It is reasonable to assume that the water would remain below 8.degree. C. for a prolonged period beyond the 95 hours, with expectations of a sustained <8.degree. C. for up to 150 hours.

An adequate freeze barrier could be provided by placing the freeze barrier between the cargo and the icepacks or other coolants.

BRIEF DESCRIPTION OF THE SEVERAL VIEWS OF THE DRAWINGS

FIG. 1. Side view: Discloses (ba) Pack in the Box™ unit (bb) protective interior sleeve, (bc) protective exterior sleeve (b) ¼" VIP, PIR, OR OTHER TRM on four sides (c) ½" VIP, PIR, or other TRM bottom base (a) TSCC environment cavity.

FIG. 2. Overhead view: Color coded schematic discloses (ba) Pack in the Box unit with red (bb) protective interior sleeve, and red (bc) protective exterior sleeve, surrounding yellow (b) ¼" VIP, PIR, OR OTHER TRM on four sides, and yellow (c) ½" VIP, PIR, OR OTHER TRM bottom base of (a) TSCC environment cavity not shown.

FIG. 3. Overall view: Color coded drawing discloses (fb) Pack in the Box logo, view of red (ba) Pack in the Box complete unit, with yellow (b) ¼" VIP, PIR, OR OTHER TRM sides, ½" VIP, PIR, OR OTHER TRM floor (not shown), enclosed in red (bb) protective interior sleeve, and red (bc) protective exterior sleeve—including bottom. (fa) TSCC logo is displayed in right lower corner FIG. 4. Discloses one piece foldable, yellow, plastic corrugated material that can be used, but is not limited to, for the (bb) protective interior sleeve, or (bc) exterior protective sleeve—depending on the width VIP, PIR, OR OTHER TRM sandwiched between layers. Also disclosed is (be) a foldable top with a hinging fold or mechanism.

FIG. 5. Discloses a side view of (ba) Pack in the Box unit made from (bb) protective interior sleeve, (bc) protective exterior sleeve, enclosing either (b) ¼" VIP, PIR, or other TRM walls, or (c) ½" VIP, PIR, or other TRM walls, with either (b) ¼" VIP, PIR, or other TRM floor (not shown), or (c) ½" VIP, PIR, OR OTHER TRM floor (not shown, and a (be) hinged top.

FIG. 6. Discloses a top view of (ba) Pack in the Box unit made from (bb) protective interior sleeve, (bc) protective exterior sleeve, enclosing either (b) ¼" VIP, PIR, or other TRM walls, or (c) ½" VIP, PIR, or other TRM walls, with either (b) ¼" VIP, PIR, or other TRM floor (not shown), or (c) ½" VIP, PIR, OR OTHER TRM floor (not shown, and a (be) hinged top, creating (a) TSCC environment cavity.

FIG. 7. Discloses a Pack in the Box Retrofit—120 hour test: 1. (bg) a common hand-held transport cooler and (ea) electronic temperature test reading device and (eb) electronic temperature testing device wires and probes; 2. open view of (bg) common hand-held transport cooler interior cargo compartment is lined with (y) icepacks, and (bf) Pack in the Box is fitted between (y) icepacks, with (y) icepacks on four sides, and (eb) electronic temperature testing device wire placed inside of interior cargo compartment of (bg) common hand-held transport cooler, the attached to (ea) electronic temperature test reading device (not shown) so as to detect air temperature inside of (bg) common hand-held cooler; 3. open view of (bg) common hand-held transport cooler interior cargo compartment is lined with (y) icepacks, and (bf) Pack in the Box is fitted between (y) icepacks, with (y) icepacks on four sides, although this view only shows three sides with icepacks, there are in fact four icepacks, against four surfaces of (bf) Pack in the Box, also shown is (eb) electronic temperature testing device wire placed inside of interior cargo compartment of (bg) common hand-held transport cooler, the attached to (ea) electronic temperature test reading device (not shown) so as to detect air temperature inside of (bg) common hand-held cooler; 4. open view of (bg) common hand-held transport cooler interior cargo compartment is lined with (y) icepacks, and open view of (bf) Pack in the Box is fitted between (y) icepacks, with (y) icepacks on four sides against four surfaces of (bf) Pack in the Box, with (bh) magnetic fastener on top and bottom of (be) lid, and inside of (a) TSCC environment is placed (bi) test decanter filled with water, and (eb) electronic temperature testing device wire and probe placed inside of (bi) and attached to (ea) (not shown), in order to monitor the interior temperature of the water inside of (bi) so as to establish if the cargo would freeze by exposure to the coolant in (y) icepacks, and also shown is (eb) electronic temperature testing device wire placed inside of interior cargo compartment of (bg) common hand-held transport cooler, the attached to (ea) electronic temperature test reading device (not shown) so as to detect air temperature inside of (bg) common hand-held cooler; 5. close-up, open view of (bg) common hand-held transport cooler interior cargo compartment is lined with (y) icepacks, and open view of (bf) Pack in the Box is fitted between (y) icepacks, with (y) icepacks on four sides against four surfaces of (bf) Pack in the Box, with (bh) magnetic fastener on top and bottom of (be) lid, and inside of (a) TSCC environment is placed (bi) test decanter filled with water, and (eb) electronic temperature testing device wire and probe placed inside of (bi) and attached to (ea) (not shown), in order to monitor the interior temperature of the water inside of (bi) so as to establish if the cargo would freeze by exposure to the coolant in (y) icepacks, and also shown is (eb) electronic temperature testing device wire placed inside of interior cargo compartment of (bg) common hand-held transport cooler, the attached to (ea) electronic temperature test reading device (not shown) so as to detect air temperature inside of (bg) common hand-held cooler; 6. open view of (bg) common hand-held transport cooler interior cargo compartment is lined with (y) icepacks, and close-up open view of (bf) Pack in the Box is fitted between (y) icepacks, with (y) icepacks on four sides against four surfaces of (bf) Pack in the Box, with (bh) magnetic fastener on top and bottom of (be) lid, and inside of (a) TSCC environment is placed (bi) test decanter filled with water, and (eb) electronic temperature testing device wire and probe placed inside of (bi) and attached to (ea) (not shown), in order to monitor the interior temperature of the water inside of (bi) so as to establish if the cargo would freeze by exposure to the coolant in (y) icepacks, and also shown is (eb) electronic temperature testing device wire placed inside of interior cargo compartment of (bg) common hand-held transport cooler, the attached to (ea) electronic temperature test reading device (not shown) so as to detect air temperature inside of (bg) common hand-held cooler.

FIG. 8. Pack in the Box Retrofit Design assembly discloses: 1. Open (bf) Pack in the Box showing (a) TSCC environment cavity, with a cutaway edge on (bj) Pack in the Box, exposing (b) ¼" VIP, PIR, OR OTHER TRM, or (c) ½" VIP, PIR, OR OTHER TRM, surrounded by (y) icepacks, positioned in (p) foam insert (includes but is not limited to VIP, PIR, OR OTHER TRM), placed inside of (ca) blue specialty hand-held transport container, with (cb) air-tight lid; 2. tightly wedging open (bf) Pack in the Box showing (a) TSCC environment cavity, with a cutaway edge on (bj) Pack in the Box, exposing (b) ¼" VIP, PIR, OR OTHER TRM, or (c) ½" VIP, PIR, OR OTHER TRM, surrounded by (y) icepacks, positioned in (p) foam insert (includes but is not limited to VIP, PIR, OR OTHER TRM), placed inside of (ca) blue specialty hand-held transport container, with (cb) air-tight lid be; 3. (ca) blue specialty hand-held transport container, showing open (bf) Pack in the Box, and (a) TSCC environment, surrounded by four (y) icepacks, fitted in (p) foam insert, with (cb) air-tight lid positioned over (ca) blue specialty hand-held transport container; 4. (ca) blue specialty hand-held transport container, with (cb) air-tight lid still off to show open (bf) Pack in the Box, and (a) TSCC environment, surrounded by four (y) icepacks, fitted in (p) foam insert; 5. closed (ca) blue specialty hand-held transport container, with (cb) air-tight lid, and (cc) Velcro closure strap and carrying shoulder strap; 6. closed (ca) blue specialty hand-held transport container, with (cb) air-tight lid, and (cc) Velcro closure strap and carrying shoulder strap, and (cd) warning sign to STOP and consider if the courier needs to open the container, thereby changing the interior temperature and affecting the performance of the (ca) blue specialty hand-held transport container, and the (bf) Pack in the Box as it maintains the air temperature of the (a) TSCC environment.

FIG. 9. Retrofit of (ca) blue specialty hand-held transport container, with closed (bf) Pack in the Box with a pull (bj) strap, being inserted into (p) foam insert of (ca) blue specialty hand-held transport container, with (bc) protective outer sleeve, surrounded by four (y) icepacks.

FIG. 10. Retrofit of (ca) blue specialty hand-held transport container, with closed (bf) Pack in the Box with a pull (bj) strap, being inserted into (p) foam insert of (ca) blue specialty hand-held transport container, with (bc) protective outer sleeve, surrounded by four (y) icepacks. Open (bf) Pack in the Box discloses (be) hinged lid, (b) ¼" VIP, PIR, OR OTHER TRM, or (c) ½" VIP, PIR, OR OTHER TRM all on five sides of (a) TSCC environment compartment—including four walls and floor, (bb) protective interior sleeve, (bc) protective exterior sleeve, and (bh) magnetic fastener.

FIG. 11. Exploded view of VIP, PIR, or other TRM layered transport container of any size, made with any size (dh) VIP, PIR, or other TRM insulative layer, with a (da) roof panel that may or may not have a (dh) VIP, PIR, or other TRM layer, a (db) top and bottom end rails, (dc) two top side rails, (dd) two rear end rails, (de) outer metal, plastic, or wooden skin on at least four sides, (df) wooden, or steel, or aluminum, or magnesium, or plastic, or other reinforcement materials aligned together or in a single sheet to form a reinforcement layer, (dg) an active layer made with either a cooling or heating element, (dh) ¼" to 12" thick VIP, PIR, or other TRM layer, or other highly insulative material, (di) surface modified interior protective layer that can be treated with a surface modifying process so as to inhibit deterioration and the growth of microbes, bacteria, pathogens, mold, mildew, improve adhesion of coatings, etc., and provide barrier resistance, hydrophobic, as well as anti-static properties, (dj) wooden or steel reinforced floor layer, (dk) at least two bottom side rails, (dl) cross member that may be made from box channel, C-channel, Z-channel, or I-beam, steel, aluminum, magnesium, or other reinforcing material, (dm) steel, reinforced plastic, wooden, aluminum, magnesium or other reinforcing material floor layer, (dm) fork lift pockets along bottom of container.

FIG. 12. Diagram of a (dn) transport container that may be but not exclusively be made from the design disclosed in FIG. 21, with (do) side opening doors, and (bf) built to scale Pack in the Box insert.

FIG. 13. Diagram of (fa) Ergonomically Designed Transport Container with (a) TSCC Environment, comprised of (fl) rigid exterior shell, made from but not limited to a surface modified material such as MMT treated plastic, or rigid foam, or metal, or aluminum, or magnesium, carbon fiber, or other structural materials and (fn) rigid interior shell, made from but not limited to a surface modified material such as MMT treated plastic, or rigid foam, or metal, or aluminum, or magnesium, or other structural materials, containing an (b) or (c) insulative layer of thermal resistant material including but not limited to VIP, PIR, or other TRM, between (fl) the rigid interior shell and (fm) the rigid exterior shell, with (fh) sealable vents molded into the front of the (fa) contoured ergonomically designed transport container, encapsulated on all exterior surfaces with (fp) a resilient polymer coating including but not limited to polyuria, polyurethane, vinyl, that may in some embodiment be applied over an additional layer of (fq) softer foam to add further cushioning properties to the (fa) transport container while in use. Said (fa) container discloses a rigid lip rim that fits air-tight when married to (fc) molded lid bottom, encapsulated with (fb) molded rigid plastic top lid that may be, but not exclusively be treated with an MMT treatment as described herein, and may be encapsulated with (fp) a resilient polymer coating; and have at least one (two shown) molded inset areas that are used for gripping the lid for removal, and for insertion into the (fa) container, fitting snuggly into the (fo) rim, and further secured by (fe) Velcro strips on both sides of the lid that attach to two (ff) Velcro tabs on either side of the (fa) container. The (fa) container has two (fg) side handles that are molded into the sides of the (fa) container as hand-grips with a hollow area where hands can fit and hold onto the (fa) securely. The (fa) is wrapped in its circumference by a composite material (fi) belt, threaded through at least four (two are shown) metal or plastic loops that are insert molded, or securely fastened into the (fa), and connected to a composite material (fj) neck or shoulder strap for ease of carrying. Said (fa) container can be retrofitted to hold at least one, (df) Pack in the Box inserted into (p) foam insert, containing (y) ice packs or other coolants, (or transversely a heat source), lined with (b) or (c) VIP, PIR, or other TRM or other thermal resistant material, maintaining the TSCC environment.

FIG. 14. Sidewall cut-away diagram of Ergonomically Designed Transport Container shows (fl) rigid exterior shell, protecting (b) or (c) thermal resistant material including but not limited to VIP, PIR, or other TRM, sandwiched against (fm) rigid interior shell, wrapped with a cushioning layer of (fq) foam, and coated on all sides by (fp) polymer coating including but not limited to polyuria, polyurethane, and other suitable coatings.

DETAILED DESCRIPTION OF THE INVENTION

One embodiment described herein, allows an exception to the freeze barrier requirement of the temperature stabilizing cargo compartment, when the desired result is to keep an already frozen cargo frozen. This exception applies in the instance where the cargo is already frozen and the requirement is to prevent the air temperature inside of the TSCC from rising above 0.degree. C. In this embodiment the TRM serves as a heat barrier only.

One embodiment of the invention maintains the constancy of the air temperature within the temperature stabilizing cargo compartment, and is not directly focused on cooling or warming the cargo itself. The cooling or warming are functions of the coolant or heat source, whereas the focus of this embodiment is the maintenance of the air enclosed in the cavity of the temperature stabilizing cargo compartment, keeping the air at a substantially constant temperature for an extended period of time, with no regard to the method of cooling or warming. This function of a thermal resistant, insulative material would stabilize the interior air environment by limiting a transference of energy between the coolant or heat source, and the air within the temperature stabilizing cargo compartment. The cargo itself would aid in stabilizing the interior air temperature as the cargo would emit a degree of energy that would be contained within the compartment.

The thermal resistant material would also provide a freeze barrier or transversely a heat barrier between the coolant or heat source, depending on the prescribed utility of the transport container.

In the preferred embodiment of this invention the construction of the temperature stabilizing cargo compartment is made from vacuum insulated panel (VIP, PIR, or other TRM) material to provide the necessary thermal resistance for stabilizing the air temperatures within the invention, as well as to serve as an excellent freeze or heat barrier between the cargo and the coolant, or transversely the heat source; thereby preserving used to preserve the cargo for extended periods of time. In this embodiment VIP, PIR, or other TRM is the thermal resistant material used for at least one surface of the temperature stabilizing cargo compartment, however the scope of this invention is not limit to the use of VIP, PIR, or other TRM only, but applies to any thermal resistant material that proves to provide adequate insulative value, and has the integrity to provide a freeze or heat barrier between the cargo and the coolant or heat source respectively.

In one embodiment of this invention, the internal air temperature of the temperature stabilizing cargo compartment constructed from TRM including but not limited to VIP, PIR, or other TRM, is maintained at a constant <8.degree. C. for extended periods of time, by means of utilizing the highly insulative properties of the TRM. In one embodiment VIP, PER, or other TRM is the preferred TRM as part of the construction of the TSCC, and is used as both an insulator in order to maintain air temperatures, and also as a freeze or heat barrier.

In the embodiment where the TRM is VIP, PIR, or other TRM, the VIP, PIR, or other TRM is encapsulated on at least three sides with a protective sleeve that prevents tearing of the outer membrane of the VIP, PIR, or other TRM material. The vacuum insulated panel (VIP, PIR, or other TRM) is a technologically advanced product that combines high R-value in a relatively thin panel. The vacuum insulated panel consists of a special core panel enclosed in an air-tight envelope, to which a vacuum is applied. This product provides an insulative value of three to seven times that of equivalent thickness of other insulation materials, such as rigid foam boards, foam beads, or fiber glass, or other forms of insulation and/or padding. Panels can be fabricated in virtually any size, making them ideal as the thermal resistant material—TRM as disclosed herein.

The core of the vacuum insulated panel is an open-cell material that allows a vacuum to be pulled on the assembly. There are several types of cores that are currently being used in vacuum insulated panels: polystyrene, polyurethane, and a combination of silica, titania and carbon. The core is wrapped in a metallic or mylar foil, and the vacuum applied. The metallic film is sealed to maintain the vacuum for a long period of time. Seals are very important, as they represent the weak point of the envelope assembly.

Because there may be some loss of insulative value as the panel ages, depending on the design of the installation, the protective sleeve must be tough, yet resistant to moisture, and easily cleaned and sanitized. Desiccants are included in the panels to remove any moisture that may occur in the panel. Special materials known as "getters" are used in the panels to absorb gases that may infiltrate the panels.

In one embodiment of this invention, the TSCC is inserted into various existing transport containers, and is not in any way limited to any size or shape or specific material as part of the construction thereof. The TSCC disclosed herein in a preferred embodiment is applied to a hand-held transport container but is not limited to such. The same invention is embodied in applications that include but are not limited to smaller shipping or hand-held containers, packaging for shipping, hand-held personal containers like cups or lunch bags, delivery containers such as shipping boxes or pizza delivery boxes or bags, or larger, truck size containers or shipping containers are not excluded, and shall apply to any enclosure to the cargo compartment of any transport container as described herein.

In one embodiment of this invention the TSCC for a transport container can be used to maintain warm air in the cargo compartment of the container by utilizing the insulative properties of VIP, PIR, or other TRM or other TRM construction. In this embodiment the internal air temperature of the TSCC can be stabilized to enable the maintenance and stabilization of said air temperature to keep the cargo warm; as in the case of certain gasses, chemicals, isotopes, or certain medical applications wherein the cargo must be kept in an environment at temperature of >8.degree. C. and at the same time not to become too warm so as to degrade the cargo.

One embodiment of the invention, a warming device, or phase change material (PCM), a thermal electric device (TED), or other heat source product, or chemical reaction, or even hot water would be used to warm the interior air of the cargo compartment so as to keep the cargo at the desired temperature, while the TRM would provide thermal resistance to outside temperatures thereby stabilizing the interior air temperature and thereby the cargo contained therein.

In the claims for all embodiments disclosed herein is the inclusion of, but are not limited to the stabilization of the air temperature itself when the cargo compartment is constructed from TRM including but not limited to VIP, PIR, or other TRM, and thereby applying the TRM technology to provide thermal stability and thereby stabilize said interior air temperatures of the cargo compartment when the interior air is exposed to a coolant, or warming device, or when the contents of the cargo compartment are already sufficiently cooled or warmed or at the temperature desired for their ultimate use, and the exterior environment may compromise the temperature of the air space within the cargo compartment described herein; and the dwell time required prior to delivery exceeds one hour and maintain the air within the temperature stabilizing cargo compartment at a substantially constant temperature for an extended period of time.

Also important as part of the claims of this patent application is the existence of a freeze or heat barrier as part of the TSCC. The properties of the TRM prevent the cargo from becoming too cold and freezing, or too warm and overheating as the cargo comes into contact with the conditioned air within the TSCC.

One embodiment of this invention applies to any size, application, or utility of a temperature stabilizing cargo compartment used to stabilize the air temperature in the interior of any said cargo compartment of any transport container in any size or shape, designed for any application or utility of said container, and as an insert that may be placed within any transport container.

Another embodiment of this invention applies to any size, application, or utility of a temperature stabilizing cargo compartment used to stabilize the air temperature in the interior of any said cargo compartment of any transport container in any size or shape, designed to include a freeze barrier or heat barrier made from any thermal resistant material, designed for any application or utility of said container, and as an insert that may be placed within any transport container.

In one embodiment of this invention, any and all vacuum insulated panel walled construction, including said VIP, PIR, or other TRM used in one or more surfaces, for the purpose of stabilizing and maintaining cargo compartment air temperature below temperatures of 8.degree. C., preventing ice melt, and preserving non-specific perishables, or transversely, sustaining adequate warmth above 8.degree. C. within the cargo compartment for certain applications is herein contemplated.

Because the TSCC can be used to transport samples and specimens, and because the container is often in an area where there is a high concentration of contagions, with limited hygienic solutions, one embodiment of the TSCC disclosed herein, is to provide a surface modified material for the interior surface wall and or other surfaces of said TSCC or the entire transport container, thereby conveying certain properties to the material from which the surface is manufactured. This can be done by several means, however for this embodiment a compound of pretreated plastics is used either as a coating or as making up the entire structure. Said composite is exposed in finely granulated form to a surface modifying gas such as sulfur trioxide, or fluorine gas, or other gases, and then exposing the now modified material to an antimicrobial agent such as silver, copper, iodine, zinc, and other chemicals that can now become part of the matrix that the composite material is made from. Another way to gain antimicrobial properties is to treat the entire sheet-stock from which the TSCC is constructed, or the completed, manufactured TSCC to the antimicrobial surface modification treatment described herein.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

For the purpose of this patent application, successful reduction of microorganisms is achieved when the populations of microorganisms are reduced by at least about 0.3 log.sub.10., for example at least about 0.3-1 log.sub.10. In this application, such a population reduction is the minimum acceptable for the processes. Any increased reduction in population of microorganisms is an added benefit that provides higher levels of protection. For example, a 3 log or greater reduction is characteristic of a hard surface sanitizer. For example, a 5 log or greater reduction is characteristic of a food contact sanitizer.

Traditional methods for the transport of various serums, samples, vaccines, and other products or materials wherein it is important to maintain a cool environment has been to place the various serums, samples, vaccines, and other products or materials in a conventional Styrofoam cooler. These coolers can become brittle and lack structural integrity thereby often resulting in the loss of valuable medicines or the compromising of various specimens. Additionally, the square edges and straight lines of containers can make them very uncomfortable and bulky to carry for longer distances and over rough terrain, especially when heavily loaded.

In one embodiment the problem of hard shelled (mettle or ridged plastic) coolers is addressed. Commonly used for the transport of various serums, samples, vaccines, and other products or materials wherein it is important to maintain a cool environment, generally have a rectangular crate-like construction. These containers usually have a hinged top lid that fits securely inside and on top of the container. The handles are usually strips of wire, rope, or plastic, or small cavity in the sides of the container, often having a small diameter or a sharp edge which can cut into or pinch the hand, making them uncomfortable to grip and carry as the containers become filled and heavy.

Most handles do not provide proper balance for carrying a loaded container. The manner in which these handles are attached to the containers, the small diameter of the grip allow the container to pivot and sway when the carrier is walking or biking, which may cause items to shift in the container or spill from it. Fragile items within the container may be damaged if shifting causes impact against a hard surface.

When a container is carried, and particularly if it is permitted to swing because of the handle design, the edges and corners of traditional rectangular containers impact the user's body. Because the length of these handles is largely dictated by the size of the container, these containers often hang low and impact the user's legs in the knee or upper shin area.

When a heavy load is carried in such known containers, a considerable torque is placed on the user's back, elbow and wrist. The orientation of the handles on existing containers tends to twist and lock the user's elbow in an uncomfortable position.

In addition to the problems related to handles, the traditional containers are not ergonomically shaped, generally having straight sides which do not conform to the curve of a user's body. If the container is held close to the body, the straight rigid sides make the containers awkward and uncomfortable to carry and walk with.

Some attempts have been made to address the deficiencies and uncomfortable nature of these containers and user's displeasure with them. Some have fit pieces of tubing, foam, vinyl, etc., over the grip portion in efforts to make the handles less painful to hold. These attempted solutions only slightly increased the diameters of the handles, did little to decrease pinching between the two handles, and completely failed to address the many other problems (such as handle length, shape of the container, point-of-contact with the body, swinging, etc.). Containers with traditional plastic handles also tend to break at the pivot points where the handles connect to the container.

SEQUENCE LISTING

Not Applicable

What is claimed is:

1. A method of making a cargo carrying enclosure for stabilizing an interior air temperature of a temperature stabilizing cargo compartment, the method of making the cargo carrying enclosure comprising:
   Providing a plurality of layers forming at least one wall, the at least one wall comprised of temperature resistant materials which insulates interior air within the temperature stabilizing cargo compartment, inhibiting heat infiltration, heat loss, vapor and moisture permeability, and stabilizing the interior air's temperature for a period of <1 to 150 hours; wherein providing the plurality of layers comprises:
   providing a first layer;
      wherein providing the first layer includes forming the first layer comprised of a micro particle material contained within a vacuum; and
   providing a second layer;
      wherein providing the second layer includes the second layer forming an interior surface of the temperature stabilizing cargo compartment and is comprised of a moisture resistant polymer, or glass, or metal or carbon; and
      wherein providing the second layer further includes exposing the second layer or the second layer's material to a fuming surface modifying gas which provides an antimicrobial agent which becomes a permanent part of a matrix of the second layer or second layer's material; and
   providing a third layer;
      wherein providing the third layer includes forming the third layer, comprised of a polymer with varying density to form a freeze barrier; and
   providing a fourth layer;
      wherein providing the fourth layer includes forming the fourth layer comprised of a cooling agent which is a phase change material.

2. The method of making the cargo carrying enclosure of claim 1, further comprising:
   inserting the temperature stabilizing cargo compartment into an existing transport container as a retrofit.

3. The method of making the cargo carrying enclosure of claim 1, further comprising:
   placing one of a medical supply, biological sample, pharmaceutical product or other temperature sensitive material within the temperature stabilizing cargo compartment whereby a constant or near constant temperature must be maintained during transportation.

4. The method of making the cargo carrying enclosure of claim 1, further comprising:
   providing a fifth layer comprised of an air hardened ridged polymer which serves as an outer layer of the cargo carrying enclosure.

5. The method of making the cargo carrying enclosure of claim 1, further comprising:
   providing a first cooling or heating apparatus located within the temperature stabilizing cargo compartment and comprises at least one of ice, a gel pack, a phase change material, energy emitting crystals, and a material causing a heat causing chemical reaction, composite material causing a chilling chemical reaction, a mechanical cooling or heating apparatus or a compressed gas.

6. The method of making the cargo carrying enclosure of claim 1, wherein exposing the second layer or the second layer's material to the fuming surface modifying gas comprises:

exposing the second layer or the second layer's material to the fuming surface modifying gas in a fuming chamber which may be, but is not limited to a fluidized bed apparatus; and measuring a dwell time and concentration level of the provided fuming surface modifying gas in order to form a treated surface that can be anywhere from 0 to 50 microns deep from the interior surface of the second layer or the second layer's material; and neutralizing an exposed material of the second layer or the second layer's material;

contacting the antimicrobial agents with the second layer or second layer's material to become the permanent part of the matrix of the second layer or second layer's material which provides properties such as antimicrobial, antistatic, hydrophobic, bondability, and barrier when desired;

wherein the antimicrobial agent of the second layer or the second layer's material is comprised of silver, copper, zinc, and other antimicrobial agent that can become a permanent part of the matrix of the second layer or second layer's material from a depth of 0 to 50 microns from the interior surface of the second layer or second layer's material which has been exposed to the fuming surface modifying gas and providing certain properties to the interior surface of the second layer or second layer's material such as antimicrobial, antistatic, hydrophobic, bondability, and barrier when desired.

7. The method of making the cargo carrying enclosure of claim 1, further comprising:

providing an absorber for absorbing vapor and liquid condensation within the temperature stabilizing cargo compartment.

8. The method of making the cargo carrying enclosure of claim 1, further comprising:

providing an upward channeled vent on the at least one wall providing a handle located on a top of the cargo carrying enclosure providing a handle located on the at least one wall.

9. A cargo carrying enclosure for stabilizing the interior temperature of temperature stabilizing cargo compartment formed by the method of claim 1.

* * * * *